United States Patent
Moriyasu

(10) Patent No.: US 11,134,912 B2
(45) Date of Patent: Oct. 5, 2021

(54) MEDICAL IMAGE DIAGNOSTIC APPARATUS

(71) Applicant: Canon Medical Systems Corporation, Otawara (JP)

(72) Inventor: Kenta Moriyasu, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 227 days.

(21) Appl. No.: 16/127,985

(22) Filed: Sep. 11, 2018

(65) Prior Publication Data

US 2019/0076110 A1   Mar. 14, 2019

(30) Foreign Application Priority Data

Sep. 11, 2017  (JP) .............................. JP2017-174015

(51) Int. Cl.
| | | |
|---|---|---|
| *A61B 8/13* | (2006.01) | |
| *A61B 6/00* | (2006.01) | |
| *G01T 1/164* | (2006.01) | |
| *G01T 1/29* | (2006.01) | |
| *A61B 6/04* | (2006.01) | |
| *A61B 6/03* | (2006.01) | |

(52) U.S. Cl.
CPC ............ *A61B 6/545* (2013.01); *A61B 6/0407* (2013.01); *A61B 6/5235* (2013.01); *G01T 1/1642* (2013.01); *G01T 1/2985* (2013.01); *A61B 6/032* (2013.01); *A61B 6/037* (2013.01); *A61B 6/461* (2013.01); *A61B 6/5241* (2013.01)

(58) Field of Classification Search
CPC ..... A61B 6/545; A61B 6/0407; A61B 6/5235; A61B 6/032; A61B 6/037; A61B 6/461; A61B 6/5241; G01T 1/1642; G01T 1/2985
See application file for complete search history.

(56) References Cited

U.S. PATENT DOCUMENTS

| 2012/0187300 A1 | 7/2012 | Gagnon |
| 2014/0148684 A1 | 5/2014 | Foo et al. |

(Continued)

FOREIGN PATENT DOCUMENTS

| JP | 2012-150114 | 8/2012 |
| JP | 2013-198747 | 10/2013 |

(Continued)

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

According to one embodiment, medical image diagnostic apparatus includes a bed, a display, and processing circuitry. The bed movably supports a top plate. The display displays a setting window for setting an acquisition time of PET event data for each acquisition area. The processing circuitry sets an acquisition time for each acquisition area in response to a setting instruction of the acquisition time for each acquisition area. The acquisition area includes a unit acquisition area or a plurality of unit acquisition areas which overlap with each other with variable overlap ratio. The unit acquisition area corresponds to a coverage of a gamma ray detector. The processing circuitry adjusts the overlap ratio of at least one of two neighboring acquisition areas so that the boundary of the neighboring acquisition areas is set to a position designated by a user.

9 Claims, 15 Drawing Sheets

(56) References Cited

U.S. PATENT DOCUMENTS

| | | |
|---|---|---|
| 2014/0270053 A1 | 9/2014 | Larson |
| 2015/0216486 A1 | 8/2015 | Moriyasu |
| 2016/0095560 A1* | 4/2016 | Nakai .................. A61B 6/4233 378/5 |
| 2017/0042492 A1 | 2/2017 | Noshi |
| 2017/0119322 A1* | 5/2017 | Yamada ................ A61B 6/032 |
| 2018/0338739 A1* | 11/2018 | Merman ............... A61B 6/488 |
| 2019/0076110 A1 | 3/2019 | Moriyasu |

FOREIGN PATENT DOCUMENTS

| | | |
|---|---|---|
| JP | 2017-37037 | 2/2017 |
| JP | 2019-49477 A | 3/2019 |

\* cited by examiner

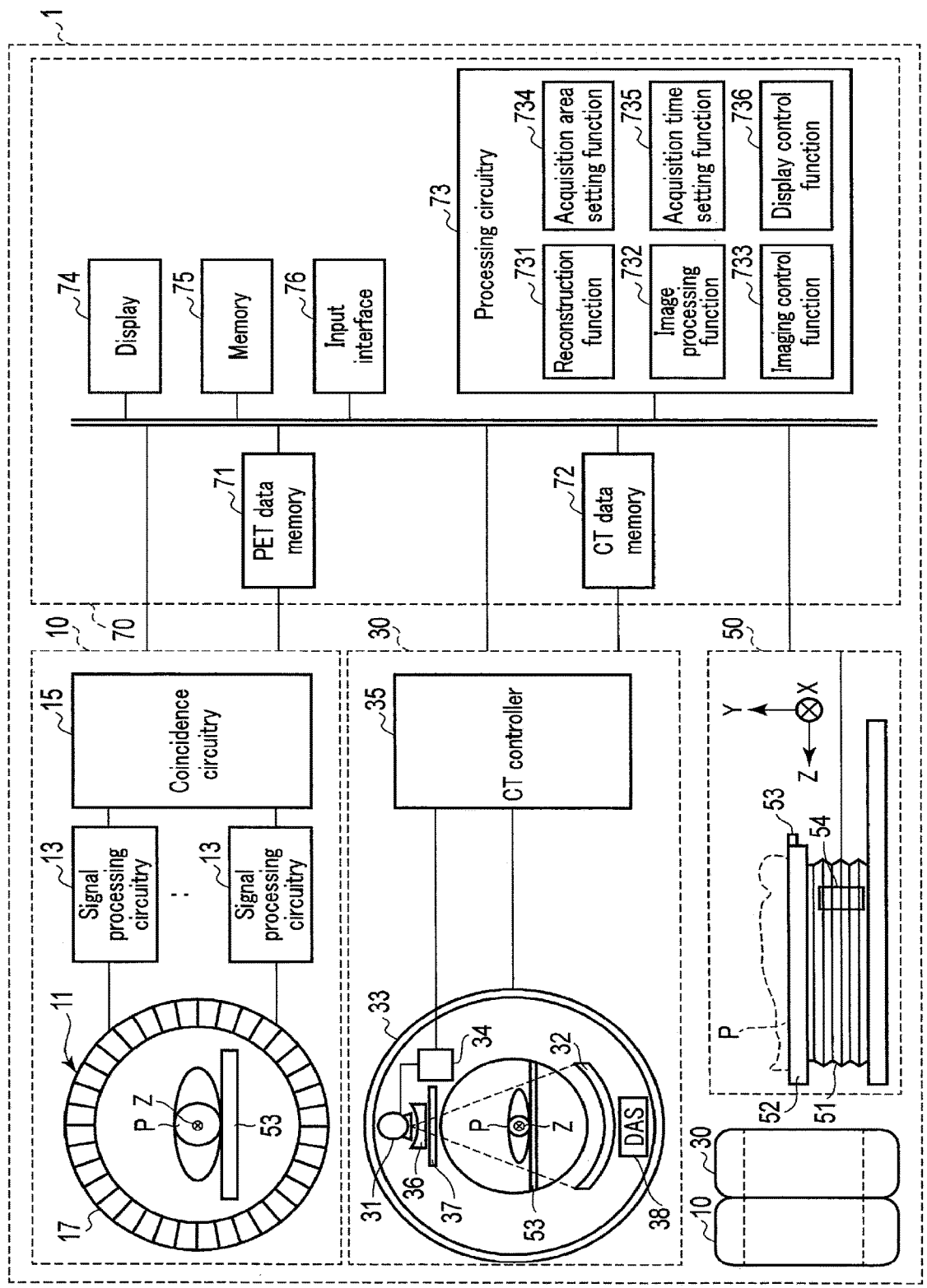
F I G. 1

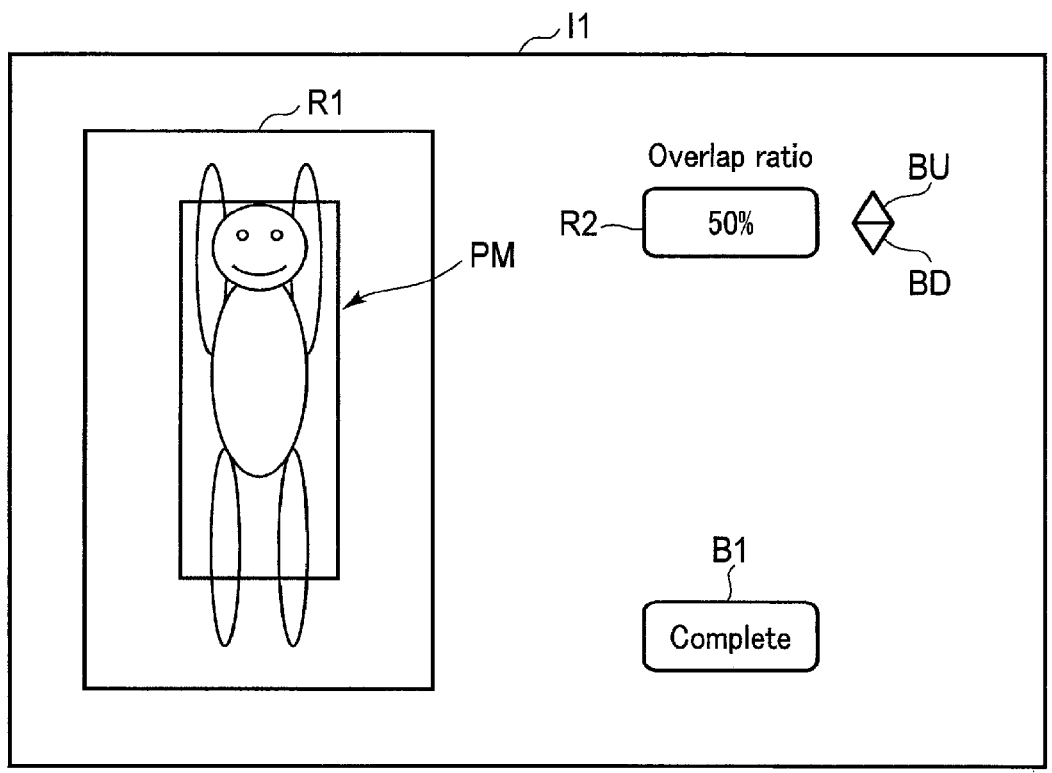
F I G. 4
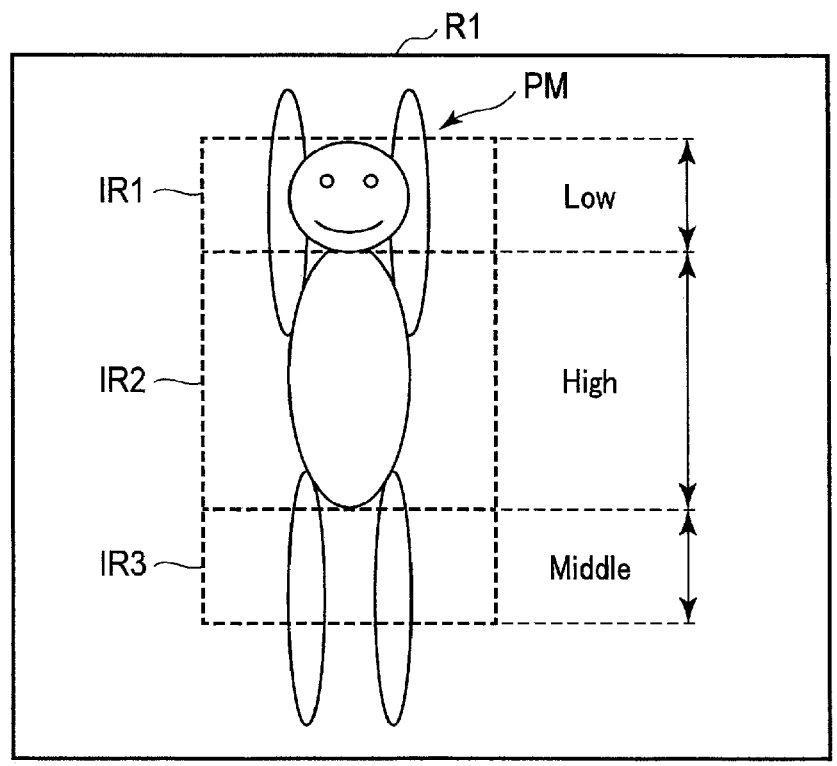
F I G. 5

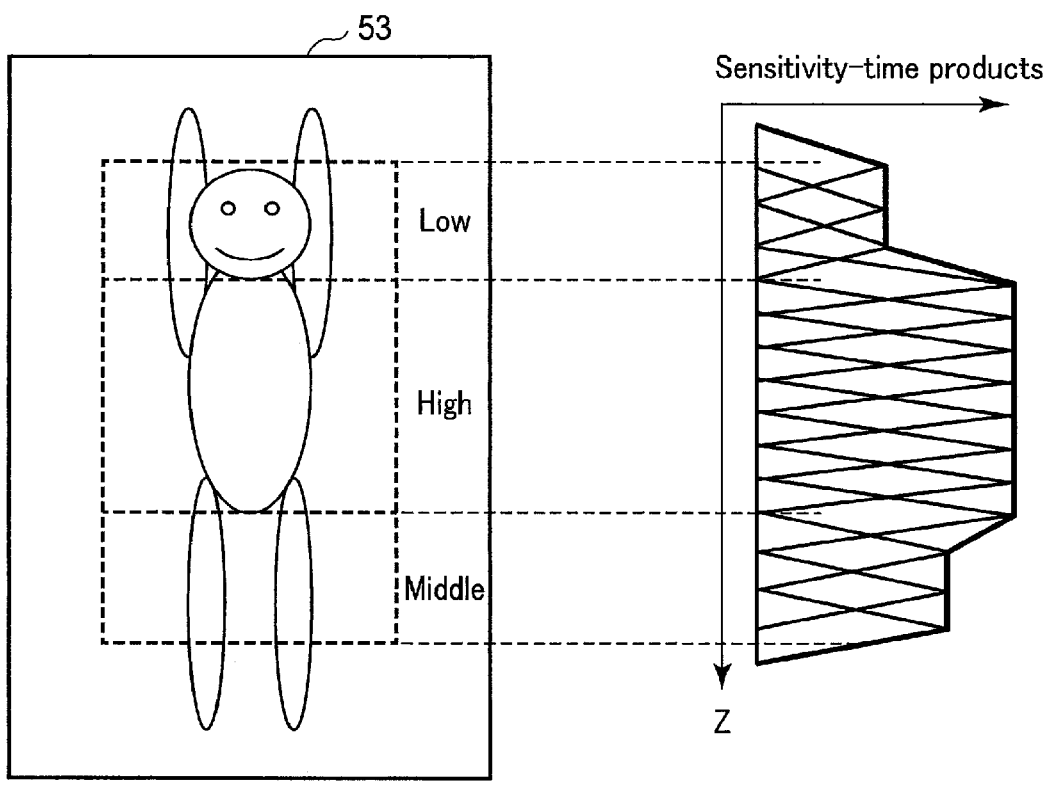
F I G. 6A    F I G. 6B

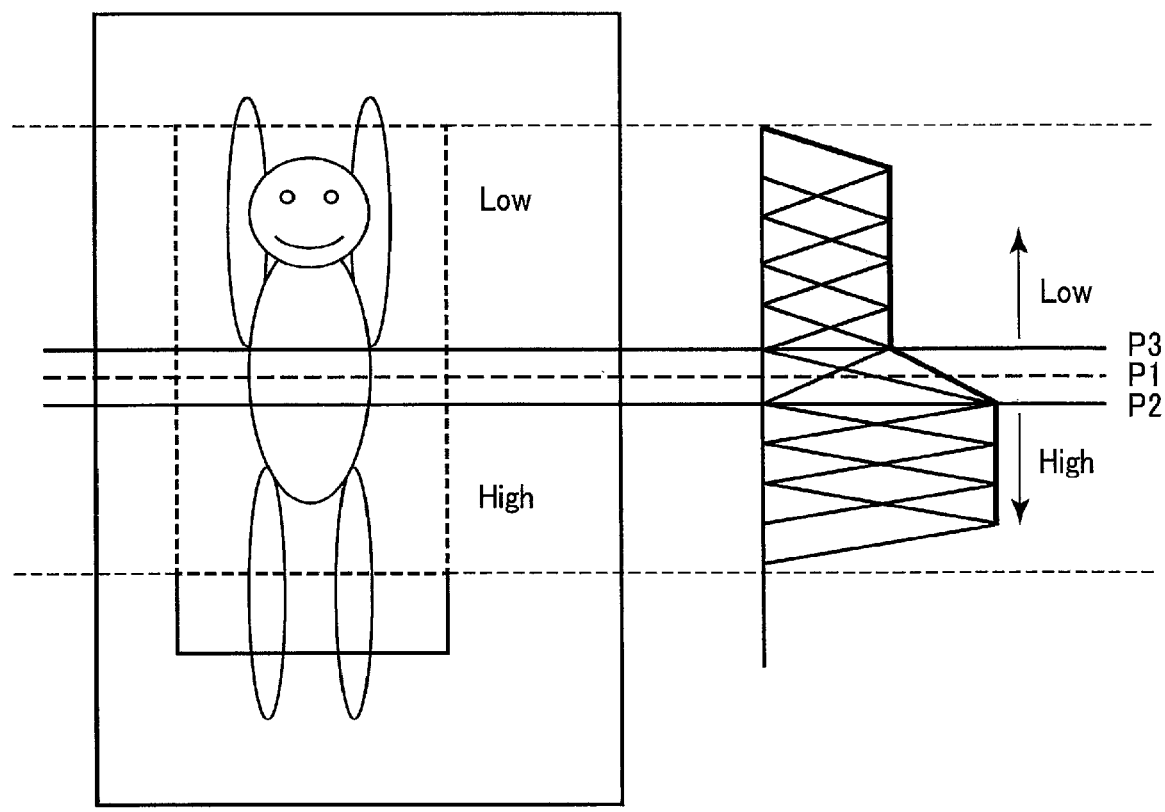
F I G. 8A                F I G. 8B

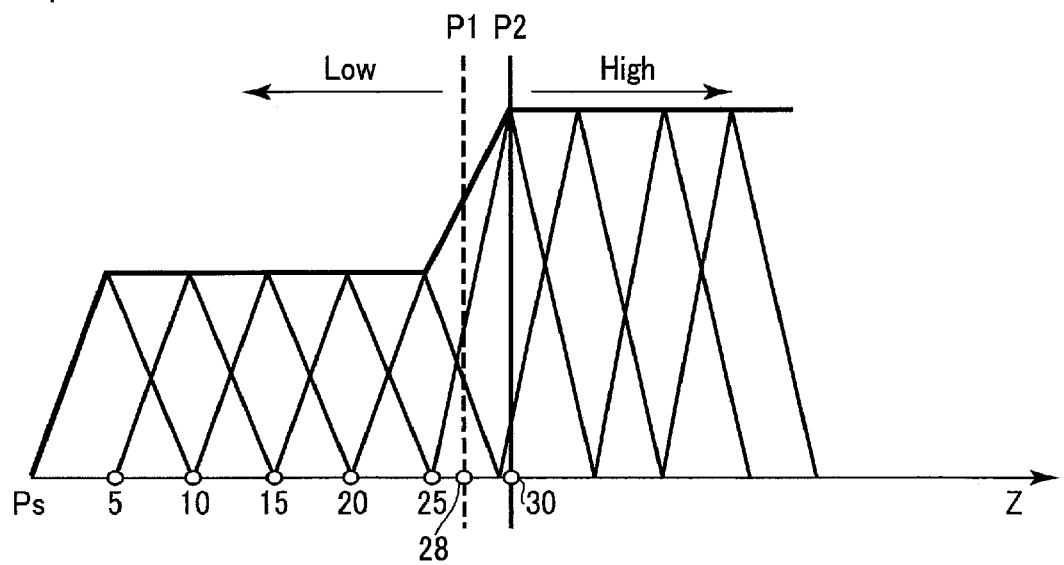
F I G. 9A
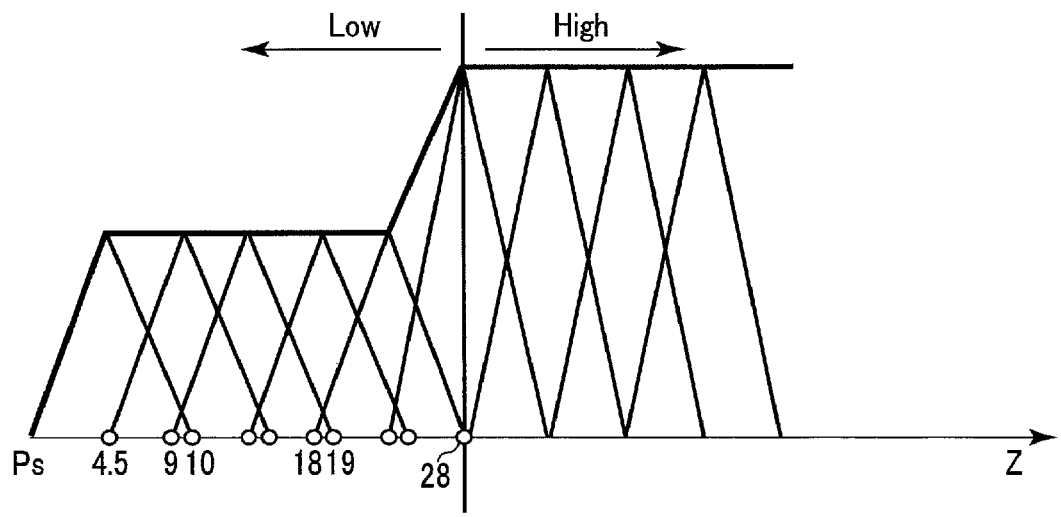
F I G. 9B

| Anatomical position | Acquisition time[s] |
|---|---|
| Brain | 30s |
| Heart | 50s |
| Bladder | 60s |

F I G. 13

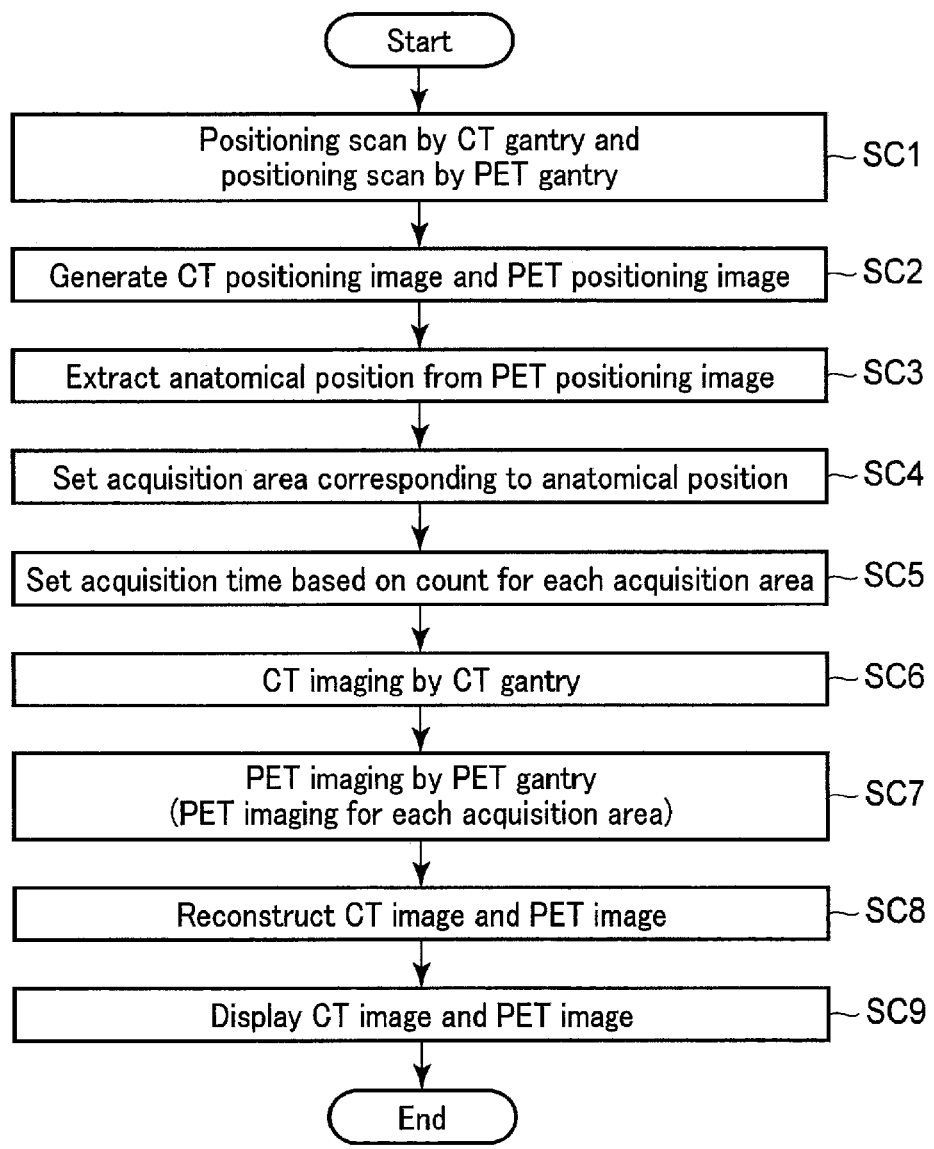
F I G. 14

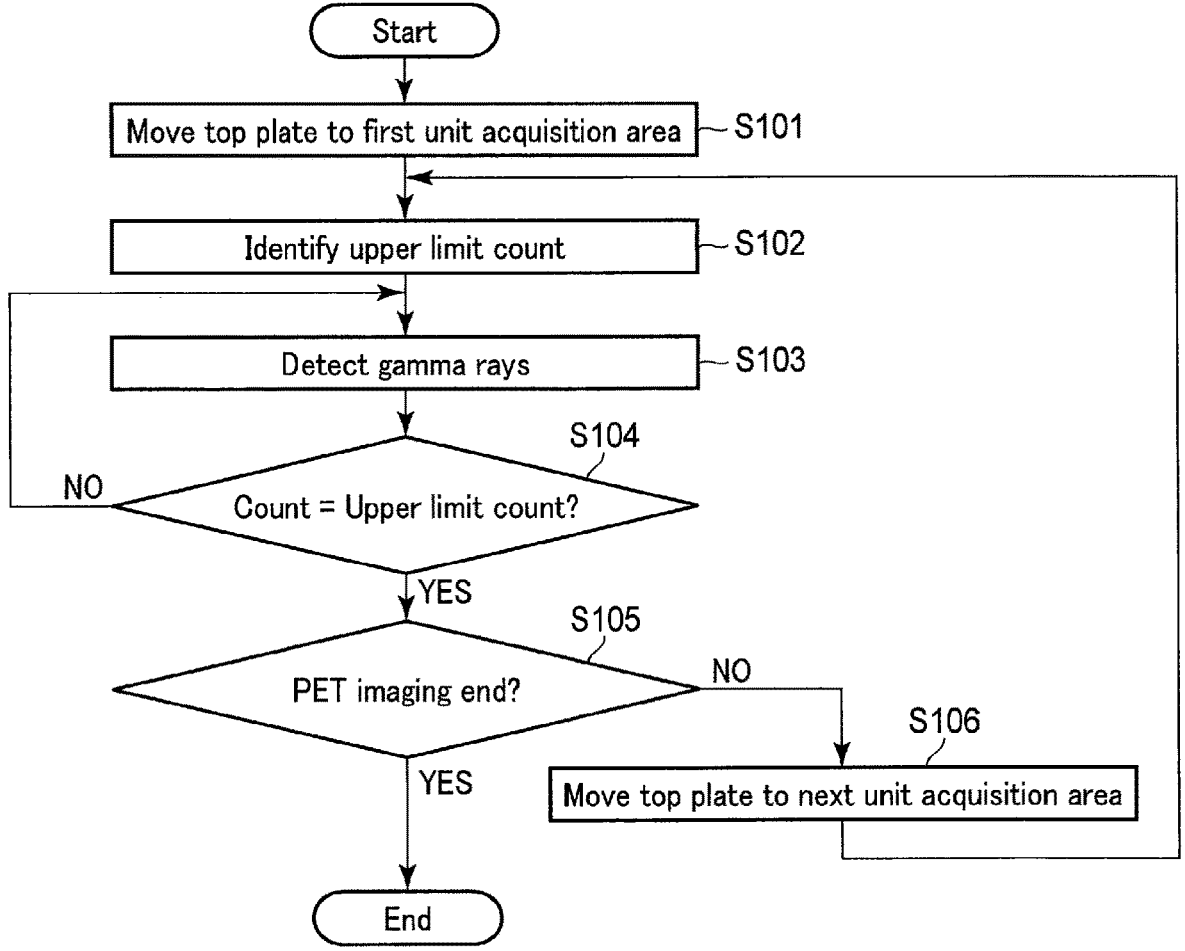
F I G. 16

MEDICAL IMAGE DIAGNOSTIC APPARATUS

CROSS-REFERENCE TO RELATED APPLICATIONS

This application is based upon and claims the benefit of priority from the prior Japanese Patent Application No. 2017-174015, filed Sep. 11, 2017 the entire contents of which are incorporated herein by reference.

FIELD

Embodiments described herein relate generally to a medical image diagnostic apparatus.

BACKGROUND

In PET (Positron Emission Tomography) imaging, intermittent movement scan (step-and-shoot acquisition) in which data acquisition is performed by intermittently moving the top plate is used. The acquisition time for intermittent movement scan is determined by setting the total acquisition time of the entire acquisition area (total acquisition time) or setting the acquisition time for each top plate position. Through this method, it is not possible to differentiate the acquisition time between portions that require high image quality and portions that do not require high image quality.

BRIEF DESCRIPTION OF THE DRAWINGS

FIG. 1 is a diagram showing the configuration of a PET/CT apparatus according to the first embodiment.

FIG. 4 shows an example of a setting window displayed in step SA1.

FIG. 5 illustrates the setting process of acquisition areas in step SA2 of FIG. 3 and the setting process of an acquisition time in step SA3 of FIG. 3.

FIGS. 6A and 6B illustrate sensitivity-time products at respective top plate positions according to the first embodiment.

FIGS. 8A and 8B are schematic diagrams showing a limitation in setting acquisition areas in the case where the overlap ratio is fixed.

FIGS. 9A and 9B are schematic diagrams showing setting of acquisition areas using VOL according to the first embodiment.

FIG. 13 illustrates an example of a portion/time table used in step SB5 of FIG. 12.

FIG. 14 is a flowchart of a typical PET/CT examination by the PET/CT apparatus according to the third embodiment.

FIG. 16 is a flowchart of a typical step-and-shoot PET imaging performed in step SD9 of FIG. 15, according to the fourth embodiment.

DETAILED DESCRIPTION

Figure 2:
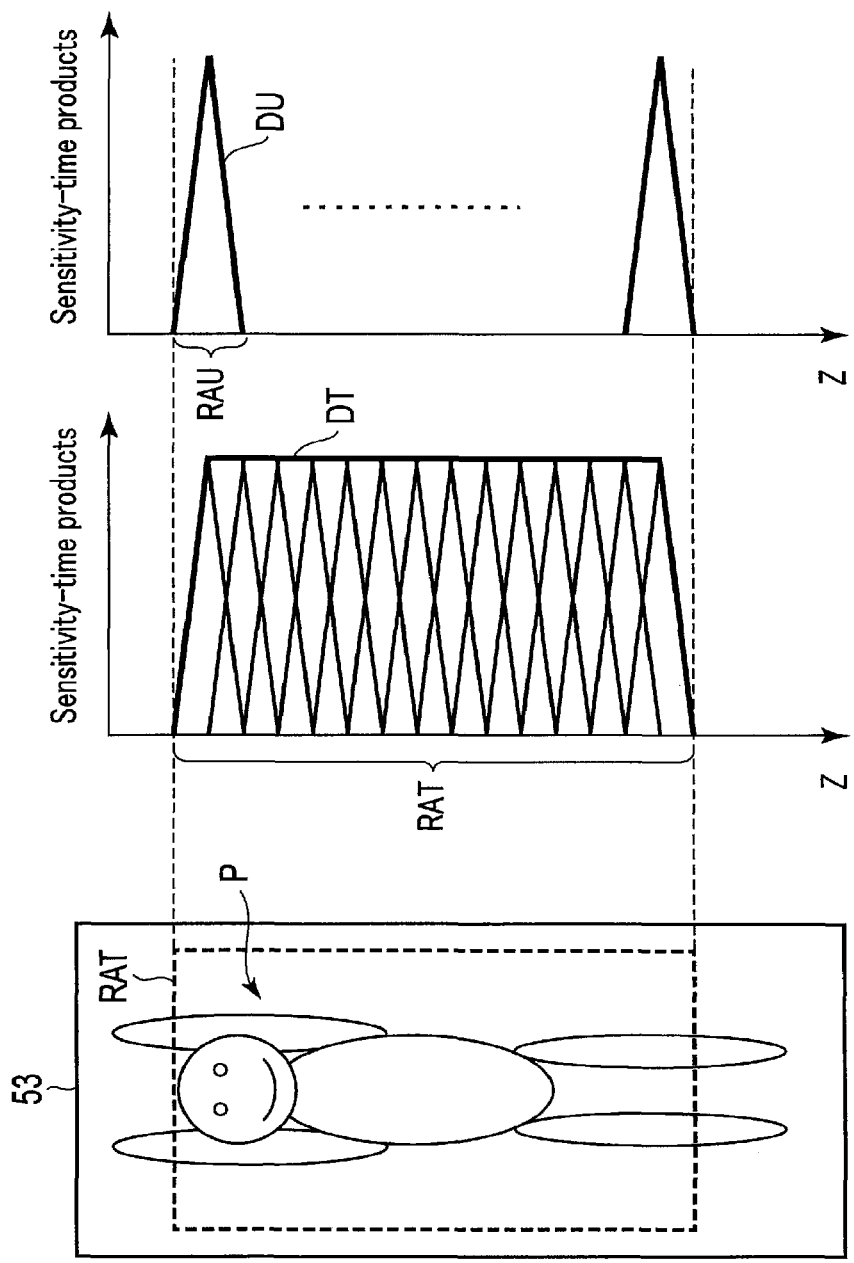
FIGS. 2A, 2B, and 2C are diagrams to explain PET imaging with step-and-shoot acquisition (step-and-shoot PET imaging) according to the first embodiment.

In general, according to one embodiment, a medical image diagnostic apparatus includes a bed, a display, and processing circuitry. The bed movably supports a top plate in a long axis direction. The display displays a setting window for setting an acquisition time of PET event data for each acquisition area arranged in the long axis direction of the top plate. The processing circuitry sets an acquisition time for each acquisition area in response to a setting instruction of the acquisition time for each acquisition area received via the setting window. The processing circuitry performs PET imaging for each acquisition area in accordance with the set acquisition time, and acquires PET event data that represents the count of gamma rays emitted from a subject. The processing circuitry generates a PET image based on the acquired PET event data. The acquisition area includes a unit acquisition area or a plurality of unit acquisition areas which overlap with each other with variable overlap ratio with regard to the long axis direction. The unit acquisition area corresponds to a coverage of a gamma ray detector included in the imaging unit. The processing circuitry adjusts the overlap ratio of at least one of two neighboring acquisition areas so that the boundary of the neighboring acquisition areas is set to a position designated by a user.

In the following descriptions, a medical image diagnostic apparatus according to the present embodiments will be explained with reference to the drawings.

The medical image diagnostic apparatus according to the present embodiments includes at least an imaging mechanism that performs PET imaging. This type of medical image diagnostic apparatus may adopt, for example, a PET apparatus that has only a PET imaging mechanism, a PET/CT apparatus that has a PET imaging mechanism and a CT (Computed Tomography) imaging mechanism, a PET/MR apparatus that has a PET imaging mechanism and a MR (Magnetic Resonance) imaging mechanism, etc. The medical image diagnostic apparatus according to the present embodiments may include an imaging mechanism that performs at least SPECT (Single Photon Emission CT) imaging. This type of medical image diagnostic apparatus may adopt, for example, a SPECT apparatus that has only a SPECT imaging mechanism, a SPECT/CT apparatus that has a SPECT imaging mechanism and a CT imaging mechanism, a SPECT/MR apparatus that has a SPECT imaging mechanism and a MR imaging mechanism, etc. The medical image diagnostic apparatus according to the present embodiments can be applied to any of these apparatuses; however, it is assumed that the PET/CT apparatus is adopted for specific explanations.

First Embodiment

FIG. 1 is a diagram showing the configuration of a PET/CT apparatus 1 according to the first embodiment. As shown in FIG. 1, the PET/CT apparatus 1 includes a PET gantry 10, a CT gantry 30, a bed 50, and a console 70. Typically, the PET gantry 10, the CT gantry 30, and the bed 50 are installed in a common examination room, and the console 70 is installed in a control room adjacent to the examination room. The PET gantry 10 is an imaging apparatus that performs PET imaging on a subject P. The CT gantry 30 is an imaging apparatus that performs X-ray CT imaging on the subject P. The bed 50 movably supports a top plate 53 on which the subject P to be imaged is placed. The console 70 is a computer that controls the PET gantry 10, the CT gantry 30, and the bed 50.

As shown in FIG. 1, the PET gantry 10 includes a detector ring 11, signal processing circuitry 13, and coincidence circuitry 15.

The detector ring 11 includes a plurality of gamma ray detectors 17 arranged on a circumference around a central axis Z. An FOV (field of view) is set in a bore of the detector ring 11. The subject P is positioned so that an imaging portion of the subject P is included in the FOV. A medicine labeled with positron-emission nuclides is applied to the subject P. Positrons emitted from positron-emission nuclides undergo mutual annihilation with surrounding electrons, and a pair of annihilation gamma rays are generate. The gamma ray detectors 17 detect annihilation gamma rays emitted from the inside of the subject P, and generate an electric signal in accordance with the amount of the detected annihilation gamma rays. For example, the gamma ray detectors 17 each include a plurality of scintillators and a plurality of photomultipliers. The scintillator receives annihilation gamma rays derived from radial isotopes inside of the subject P, and generates light. The photomultiplier generates an electric signal in accordance with the amount of light. The generated electric signal is supplied to the signal processing circuitry 13.

The signal processing circuitry 13 generates a single event data based on the electric signals from the gamma ray detectors 17. Specifically, the signal processing circuitry 13 performs detection time measurement process, position calculation process, and energy calculation process. The signal processing circuitry 13 is implemented by an ASIC (Application Specific Integrated Circuit), an FPGA (Field Programmable Gate Array), a CPLD (Complex Programmable Logic Device), or an SPLD (Simple Programmable Logic Device), which is configured to be able to execute a detection time measurement process, position calculation process, and energy calculation process.

Via the detection time measurement process, the signal processing circuitry 13 measures a detection time in which gamma rays are detected by gamma ray detectors 17. Specifically, the signal processing circuitry 13 monitors a peak value of electric signals from the gamma ray detectors 17, and measures a time when the peak value exceeds a predetermined threshold value as a detection time. In other words, the signal processing circuitry 13 electrically detects annihilation gamma rays by detecting that the peak value exceeds the threshold value. Via the position calculation process, the signal processing circuitry 13 calculates an incidence position of the annihilation gamma rays based on the electric signals from the gamma ray detectors 17. The incidence position of annihilation gamma rays corresponds to positional coordinates of a scintillator to which the annihilation gamma rays enter. Via the energy calculation process, the signal processing circuitry 13 calculates an energy value of the detected annihilation gamma rays based on the electric signals from the gamma ray detectors 17. Data of the detection time, data of positional coordinates, and data of the energy value with regard to a single event are associated with each other. A combination of data of the energy, data of positional coordinates, and data of the detection time with regard to a single event is referred to as single event data. The single event data is sequentially generated every time annihilation gamma rays are detected. The generated single event data is supplied to the coincidence circuitry 15.

The coincidence circuitry 15 performs coincident processing to the single event data supplied from the signal processing circuitry 13. The coincidence circuitry 15 is implemented by an ASIC, a FPGA, a CPLD, or an SPLD, which is configured to be above to execute coincident processing, as a hardware resource. In the coincident processing, the coincidence circuitry 15 subsequently determines single event data related to two single events settled in a predetermined time window from among subsequently supplied signal event data. The specified pair of single events are estimated to be derived from annihilation gamma rays generated by the same annihilation gamma rays. The pair of single events are referred to as a coincidence event. A line connecting a pair of gamma ray detectors 17 (more specifically, scintillators) that have detected the annihilation gamma rays is referred to as an LOR (Line of Response). The event data related to the pair events composing the LOR is referred to as a coincidence event data. The coincidence event data and the single event data are transmitted to the console 70. When the coincidence event data and the single event data do not need to be distinguished from each other, they are referred to as PET event data.

In the aforementioned configuration, the signal processing circuitry 13 and the coincidence circuitry 15 are included in the PET gantry 10, but the present embodiment is not limited thereto. For example, only the coincidence circuitry 15, or both of the signal processing circuitry 13 and the coincidence circuitry 15 may be included in an apparatus independent from the PET gantry 10. A single coincidence circuitry 15 may be provided for all of the multiple units of signal processing circuitry 13 included in the PET gantry 10, or may be provided for each of the grouped multiple units of signal processing circuitry 13 included in the PET gantry 10.

As shown in FIG. 1, the CT gantry 30 includes an X-ray tube 31, an X-ray detector 32, a rotation frame 33, a high-voltage X-ray device 34, a CT controller 35, a wedge 36, a collimator 37, and a DAS (Data Acquisition System) 38.

The X-ray tube 31 generates X-rays. Specifically, the X-ray tube 31 includes a vacuum tube with a cathode that generates thermoelectrons and an anode that generates X-rays by receiving the thermoelectrons traveled from the cathode. The X-ray tube 31 is connected to a high-voltage X-ray device 34 via a high voltage cable. The high-voltage X-ray device 34 applies a tube voltage between the cathode and the anode. Thermoelectrons travel from the cathode to the anode upon application of the tube voltage. A tube current flows via thermoelectrons traveling from the cathode to the anode. Via application of high-voltage and supplement of a filament current by the high-voltage X-ray device 34, thermoelectrons travel from the cathode to an anode, and collide with the anode, and X-rays are generated.

The X-ray detector 32 detects X-rays generated from the X-ray tube 31 that have passed through the subject P, and outputs an electric signal in accordance with the amount of the detected X-rays to the DAS 38. The X-ray detector 32 has a structure in which X-ray detection element arrays, in which a plurality of X-ray detection elements are arranged in a channel direction, are arranged in a slice direction (row direction). The X-ray detector 32 is, for example, an indirect conversion type detector which includes a grid, a scintillator array, and an optical sensor array. The scintillator array includes a plurality of scintillators. The scintillator outputs light of the amount in accordance with the amount of applied X-rays. The grid is arranged at an X-ray incident surface side of the scintillator array, and includes an X-ray shielding plate that absorbs scattered X-rays. The optical sensor array converts the light into an electric signal in accordance with the light amount from the scintillator. For example, a photodiode or a photomultiplier is adopted as the optical sensor. The X-ray detector 32 may be a direct conversion type detector (semiconductor detector) including semiconductor elements that convert applied X-rays into electric signals.

The rotation frame 33 is an annular-shaped frame that supports the X-ray tube 31 and the X-ray detector 32 rotatably around a rotation axis Z. Specifically, the rotation frame 33 supports the X-ray tube 31 and the X-ray detector 32 so as to face each other. The rotation frame 33 is rotatably supported by a stationary frame (not illustrated) about the rotation axis Z. As the rotation frame 33 rotates about the rotation axis Z via the control of the CT controller 35, the X-ray tube 31 and the X-ray detector 32 rotates about the rotation axis Z. The rotation frame 33 rotates about the rotation axis Z at a predetermined angular velocity upon receiving power from a driver of the CT controller 35. A field of view (FOV) is set in the bore of the rotation frame 33.

In the present embodiments, the rotation axis of the rotation frame 33 or the longitudinal direction of the top plate 53 of the bed 50 is defined as a Z-axis direction, an axial direction which is orthogonal to the Z-axis direction and horizontal to the floor is defined as an X-axis direction, and an axial direction which is orthogonal to the Z-axis direction and vertical to the floor is defined as a Y-axis direction in the non-tilt state.

The high-voltage X-ray device 34 includes a high voltage generator that includes electric circuitry such as a transformer, a rectifier, etc., and generates a high voltage to be applied to the X-ray tube 31 and a filament current to be supplied to the X-ray tube 31; and an X-ray controller that controls an output voltage in accordance with the X-rays that the X-ray tube 31 emits. The high voltage generator may be a transformer type generator, or an inverter type generator. The high-voltage X-ray device 34 may be provided in the rotation frame 33 in the CT gantry 30, or in the stationary unit (not illustrated) in the CT gantry 30.

The wedge 36 adjusts the dose of X-rays to be applied to the subject P. Specifically, the wedge 36 attenuates X-rays so that the dose of X-rays to be applied to the subject P from the X-ray tube 31 exhibits a predetermined distribution. For example, a metallic plate of aluminum, etc., such as a wedge filter or a bow-tie filter, is applied to the wedge 36.

The collimator 37 limits an irradiation range of X-rays that have passed the wedge 36. The collimator 37 slidably supports a plurality of lead plates that shield X-rays, and adjusts the shape of a slit formed by the plurality of lead plates.

The DAS 38 reads from the X-ray detector 32 an electric signal in accordance with the dose of X-rays detected by the X-ray detector 32, amplifies the read electric signal with a variable amplification rate, and integrates the electric signal over a view period to acquire CT raw data with a digital value in accordance with the dose of X-rays over the view period. The DAS 38 is implemented, for example, by an ASIC on which a circuit element capable of generating CT raw data is mounted. The CT raw data is transmitted to the console 70 via a non-contact data transmission unit, etc.

The CT controller 35 controls the high-voltage X-ray device 34 or the DAS 38 to execute X-ray CT imaging in accordance with an imaging control function 733 of processing circuitry 73 of the console 70. The CT controller 35 includes processing circuitry having a CPU, etc., and a driver such as a motor or an actuator, etc. The processing circuitry includes, as hardware resources, a processor such as a CPU, an MPU, etc. and a memory such as a ROM, a RAM, etc. The CT controller 35 may be implemented by an ASIC, an FPGA, a CPLD, or an SPLD.

The CT gantry 30 may adopt a Rotate/Rotate type (third generation CT) in which both the X-ray generator and the X-ray detector integrally rotate around the subject, or a Stationary/Rotate type (fourth generation CT) in which multiple X-ray detection elements arranged in a form of a ring are stationary, and only the X-ray generator rotates around the subject, etc., and any types can be adopted to an embodiment.

As shown in FIG. 1, the subject P to be scanned is placed on the bed 50, and the bed 50 moves the subject P. The bed 50 is commonly used for the PET gantry 10 and the CT gantry 30.

The bed 50 includes a base 51, a support frame 52, a top plate 53, and a bed motor 54. The base 51 is provided on the floor. The base 51 is a housing that movably supports the support frame 52 in the vertical direction (Y-axis direction) relative to the floor. The support frame 52 is a frame provided above the base 51. The support frame 52 enables the top plate 53 to be slid along the central axis Z. The top plate 53 is a plate with flexibility on which the subject P is placed.

The bed motor 54 is housed, for example, in the housing of the bed 50. The bed motor 54 is a motor or an actuator that generates power to move the support frame 52 and the top plate 53 on which the subject P is placed. The bed motor 54 operates under the control of the console 70, etc.

The PET gantry 10 and the CT gantry 30 are arranged so that the central axis Z of the bore of the PET gantry 10 and the central axis Z of the bore of the CT gantry 30 essentially agree with each other. The bed 50 is arranged so that the long axis of the top plate 53 is parallel to the central axis Z of the bore of the PET gantry 10 and the CT gantry 30. The CT gantry 30 and the PET gantry 10 are sequentially arranged, the CT gantry 30 being closer to the bed 50.

As shown in FIG. 1, the console 70 includes a PET data memory 71, a CT data memory 72, the processing circuitry 73, a display 74, a memory 75, and an input interface 76. Data communication is performed between the PET data memory 71, the CT data memory 72, the processing circuitry 73, the display 74, the memory 75, and the input interface 76 via a bus.

The PET data memory 71 is a storage device that stores single event data and coincidence event data transmitted from the PET gantry 10. The PET data memory 71 is a storage device such as an HDD, an SSD, or an integrated circuit storage unit, etc.

The CT data memory 72 is a storage device that stores CT raw data transmitted from the CT gantry 30. The CT data memory 72 is a storage device such as an HDD, an SSD, or an integrated circuit storage unit, etc.

The processing circuitry 73 includes a processor such as a CPU, an MPU, or a GPU (Graphics Processing Unit), etc. and a memory such as a ROM or a RAM, etc. as hardware resources. The processing circuitry 73 executes various types of programs to implement a reconstruction function 731, an image processing function 732, the imaging control function 733, an acquisition area setting function 734, an acquisition time setting function 735, and a display control function 736. The reconstruction function 731, the image processing function 732, the imaging control function 733, the acquisition area setting function 734, the acquisition time setting function 735, and the display control function 736 may be implemented either by the processing circuitry 73 on a single substrate, or by the processing circuitry 73 on a plurality of substrates.

Via the reconstruction function 731, the processing circuitry 73 reconstructs a PET image representing a distribution of the positron-emission nuclides applied to the subject P, based on the coincidence event data transmitted from the PET gantry 10. The processing circuitry 73 also reconstructs a CT image representing a space distribution of CT values relating to the subject P, based on the CT raw data transmitted from the CT gantry 30. The known image reconstruction algorithm such as an FBP (Filtered Back Projection) method or a successive approximation reconstruction method, may be adopted. The processing circuitry 73 is capable of generating a positioning image related to PET based on the PET event data, or generating a positioning image related to CT based on the CT raw data.

Via the image processing function 732, the processing circuitry 73 performs various types of image processing to the PET image and the CT image reconstructed via the reconstruction function 731. For example, the processing circuitry 73 performs three-dimensional image processing, such as volume rendering, surface volume rendering, pixel value projection processing, MPR (Multi-Planer Reconstruction) processing, and CPR (Curved MPR) processing, etc. to the PET image and the CT image to generate a display image.

Via the imaging control function 733, the processing circuitry 73 synchronously controls the PET gantry 10 and the bed 50 to perform PET imaging. The PET imaging according to the present embodiment is assumed to be an intermittent movement scan (step-and-shoot acquisition) in which PET event data is acquired for each acquisition area while the top plate 53 is intermittently moved. The processing circuitry 73 synchronously controls the CT gantry 30 and the bed 50 to perform CT imaging. When the PET imaging and the CT imaging are continuously performed, the PET gantry 10, the CT gantry 30, and the bed 50 are synchronously controlled. The processing circuitry 73 is also capable of performing a positioning scan by the PET gantry 10 (hereinafter referred to as "PET positioning scan") and a positioning scan by the CT gantry 30 (hereinafter referred to as "CT positioning scan"). The processing circuitry 73 synchronously controls the PET gantry 10 and the bed 50 to perform a PET positioning scan. The processing circuitry 73 synchronously controls the CT gantry 30 and the bed 50 to perform a CT positioning scan.

Via the acquisition area setting function 734, the processing circuitry 73 sets an acquisition area related to the PET imaging. The acquisition area is set, for example, in response to a user's instruction through the input interface 76 input via the setting window displayed by the display control function 736.

Via the acquisition time setting function 735, the processing circuitry 73 sets an acquisition time for each acquisition area set via the acquisition area setting function 734. The acquisition time is set, for example, in response to a user's instruction through the input interface 76 input via the setting window displayed by the display control function 736.

Via the display control function 736, the processing circuitry 73 displays various types of information on the display 74. For example, the processing circuitry 73 displays the PET image and the CT image reconstructed via the reconstruction function 731. The processing circuitry 73 also displays the setting window of the acquisition area and the acquisition time.

The display 74 displays various types of information under control of the processing circuitry 73 via the display control function 736. For example, a CRT display, a liquid crystal display, an organic EL display, an LED display, a plasma display, or any other display known in this technical field may be adopted as the display 74.

The memory 75 is a storage device such as an HDD, an SSD, or an integrated circuit storage device, etc., configured to store various kinds of information. The memory 75 may be a drive, etc. configured to read and write various kinds of information with respect to a portable storage medium such as a CD-ROM drive, a DVD drive, or a flash memory, etc.

The input interface 76 inputs various instructions from a user. Specifically, the input interface 76 is coupled to an input device. A keyboard, a mouse, a trackball, a joystick, or switches, etc. may be used as the input device. The input interface 76 supplies an output signal from the input device to the processing circuitry 73 via a bus.

Next, the operation example of the PET/CT apparatus 1 according to the present embodiment will be described.

The PET/CT apparatus 1 according to the first embodiment accomplishes simple setting of an acquisition area and an acquisition time for step-and-shoot PET imaging.

FIGS. 2A, 2B, and 2C are diagrams to explain step-and-shoot PET imaging. FIG. 2A is a schematic plan view of the subject P placed on the top plate 53, and FIG. 2B is a graph showing a distribution of sensitivity-time products of the entire PET imaging. FIG. 2C is a graph showing a distribution of sensitivity-time products for a top plate stationary position.

As shown in FIG. 2A, the subject P is placed on the top plate 53. The acquisition range of the entire PET imaging (hereinafter referred to as "entire acquisition range RAT") is set to substantially cover the entire body of the subject P. The acquisition range relative to the Z-axis direction of the PET event data corresponds to a coverage relative to the Z-axis direction of the gamma ray detectors 17. Accordingly, in order to acquire PET event data over the wide acquisition range RAT, the step-and-shoot PET imaging that acquires PET event data while intermittently moving the top plate 53 in the Z-axis direction is adopted.

A triangle DU shown in FIG. 2C indicates a sensitivity-time product distribution of the gamma ray detectors 17 at a corresponding stationary position of the top plate 53 (hereinafter referred to as "top plate stationary position"). The length of the base of a triangle DU (the length in the Z-axis direction) indicates a coverage RAU relative to the Z-axis direction of the gamma ray detectors 17. The sensitivity-time products are defined by products of the sensitivity of the gamma ray detectors 17 and an acquisition time. The center of the coverage relative to the Z-axis direction of the gamma ray detectors 17 exhibits the highest sensitivity, and the sensitivity decreases going away from the center toward an end. In the present embodiment, a coverage in the Z-axis direction of the gamma ray detectors 17 at a top plate stationary position is referred as a unit acquisition area RAU.

As shown in FIG. 2B, in step-and-shoot acquisition, a plurality of unit acquisition areas RAU are set over the entire acquisition range RAT so that two neighboring unit acquisition areas RAU overlap with each other in the Z-axis direction. Namely, PET event data is acquired by stopping the top plate 53 at each of a plurality of top plate stationary positions corresponding to respective unit acquisition areas RAU. In the present embodiment, a ratio of an area where two neighboring unit acquisition areas RAU overlap with each other to an area of a unit acquisition area RAU is referred to as an overlap ratio. For example, as shown in FIG. 2B, if the overlap ratio is 50%, a half of a unit acquisition area RAU overlap with an adjacent unit acquisition area in the Z-axis direction. The sensitivity-time product distribution DT of the entire PET imaging corresponds to the sum of the sensitivity-time products of triangles DU corresponding to all unit acquisition areas RAU included in the entire acquisition range RAT.

In FIGS. 2A, 2B, and 2C, an acquisition time for each top plate stationary position is assumed to be the same. The PET/CT apparatus 1 according to the first embodiment uses a VBT (Variable Bed Time) in which an acquisition time can be set for each top plate stationary position, and provides a user interface with which a user can set an acquisition time, etc. simply and swiftly with the VBT. In the VBT according to the first embodiment, an acquisition time is set for each acquisition area. The acquisition area is defined by a unit acquisition area or a set of unit acquisition areas which are spatially consecutive in the Z-axis direction, and have the same acquisition time. The details of the acquisition area will be described later.

Figure 3:
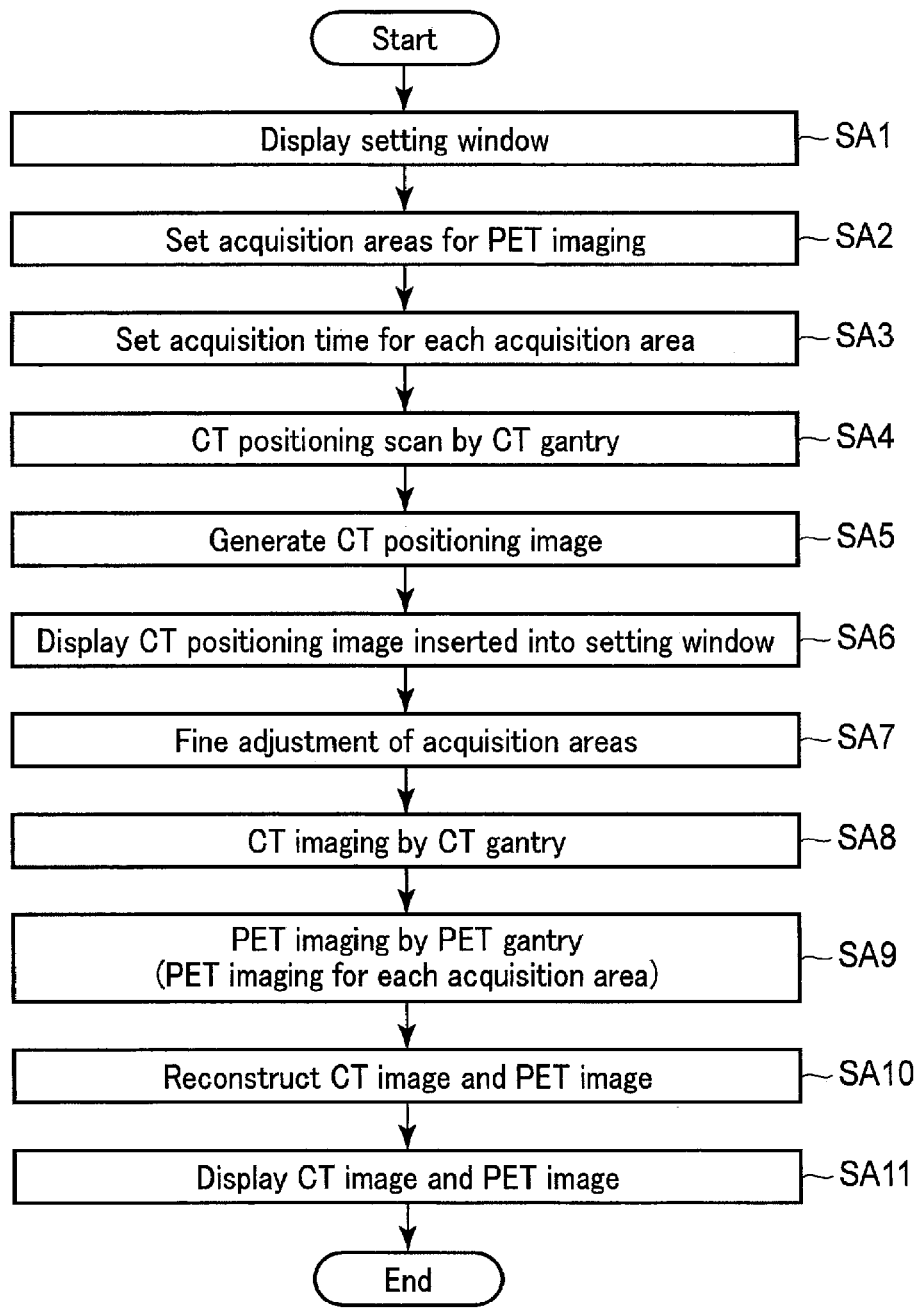
FIG. 3 is a flowchart of a typical PET/CT examination by the PET/CT apparatus according to the first embodiment.

FIG. 3 is a flowchart of a typical PET/CT examination by the PET/CT apparatus 1 according to the first embodiment. The PET/CT examination indicates a medical examination in which both PET imaging and CT imaging are performed.

First, the processing circuitry 73 executes the display control function 736 (step SA1). In step SA1, the processing circuitry 73 displays a setting window on the display 74 as a user interface through which an acquisition area and an acquisition time for the step-and-shoot PET imaging are set.

FIG. 4 shows an example of a setting window I1 displayed in step SA1. As shown in FIG. 4, the setting window I1 includes a setting region R1 of an acquisition area and an acquisition time. In the setting region R1, a subject model PM which is a model of a subject is displayed. The subject model PM may be an elaborate model which represents a physique of an actual subject P, or a model of a standard physique. The setting window I1 includes an overlap ratio display region R2 Buttons BU and BD with which the overlap ratio is adjusted are displayed next to the display region R2. The button BU is to increase the overlap ratio by a definite range such as 1%, 5%, etc. The button BD is to decrease the overlap ratio by a definite range such as 1%, 5%, etc. The setting window I1 includes a completion button B1 through which a completion of setting an acquisition area is instructed in step SA2, and a completion of setting an acquisition time is instructed in step SA3.

After step SA1, the processing circuitry 73 executes the acquisition area setting function 734 (step SA2). In step SA2, the processing circuitry 73 sets acquisition areas for the PET imaging in response to a user's instruction through the input interface 76 input in the setting window displayed in step SA1. The Step SA2 will be described later in detail.

After step SA2, the processing circuitry 73 executes the acquisition time setting function 735 (step SA3). In step SA3, the processing circuitry 73 sets an acquisition time for each acquisition area set in step SA2.

FIG. 5 illustrates the setting process of acquisition areas in step SA2 and the setting process of an acquisition time in step SA3. As shown in FIG. 5, in the setting region R1, an indicator IRn (n is an integer representing the acquisition area number) which indicates an acquisition area is superimposed on the subject model PM. The acquisition area is a unit acquisition area or a set of unit acquisition areas which are spatially consecutive in the Z-axis direction, and have the same acquisition time. The number, positions, and ranges of acquisition areas can be discretionarily set in accordance with an adjustment instruction to the indicator IRn by a user through the input interface 76. In other words, the processing circuitry 73 sets the number, positions and ranges of the acquisition areas in response to the adjustment instruction for division of the acquisition area received via the setting window I1. Specifically, in the case where a discretionary position in the setting region R1 is clicked by a mouse, etc., the indicator IRn is displayed at the clicked position. The position and range of the displayed indicator IRn can be changed discretionarily by a drag-and-drop operation, etc. The processing circuitry 73 sets a top plate position (Z-axis direction position) corresponding to the indicator IRn as an acquisition area.

If the acquisition area is set, an acquisition time is set for the acquisition area. In the first embodiment, a user interface through which a user can easily set an acquisition time is provided. For example, predetermined levels are prepared for an acquisition time. The predetermined levels include, for example, a short time (Low), a standard time (Middle), and a long time (High). A predetermined default value is set for each of the levels, "short time", "standard time", and "long time". For example, the "short time" is set as 30 seconds, the "standard time" is set as one minute, and the "long time" is set as one and a half minutes. An acquisition time can be discretionarily allocated to each acquisition area in accordance with an instruction by a user through the input interface 76. For example, upon a click on an acquisition area by a mouse, the acquisition time is allocated cyclically in order of "short time", "standard time", and "long time", to the clicked acquisition area.

In this case, in each indicator IRn of the acquisition area, visual information corresponding to "short time", "standard time", and "long time" allocated to the indicator IRn may be displayed. For example, as shown in FIG. 5, text information of "Low" representing "short time", "Middle" representing "standard time", and "High" representing "long time" may be displayed next to each indicator IRn, as the visual information. The indicator IRn of the acquisition area may be colored in a predetermined color corresponding to "short time", "standard time", or "long time" allocated to the indicator IRn. For example, an acquisition area to which "short time" is allocated may be colored in blue, an acquisition area to which "standard time" is allocated may be colored in green, and an acquisition area to which "long time" is allocated may be colored in red. The processing circuitry 73 determines the acquisition time allocated to each acquisition area as an acquisition time for the acquisition time.

According to the first embodiment, the acquisition area and the acquisition time can be set by a visually clear and simple operation via the user interface. In addition, since the acquisition time is determined by selecting a desired acquisition time from among the predetermined levels of acquisition time, the acquisition time can be simply and swiftly set.

FIGS. 6A and 6B illustrate sensitivity-time products at respective top plate positions. FIG. 6A is a schematic plan view of the subject P placed on the top plate 53, and FIG. 6B is a graph indicating sensitivity-time products at respective top plate positions. As shown in FIG. 6A, it is assumed that an acquisition area of "short time" corresponding to a head of the subject P, an acquisition area of "long time" corresponding to a torso of the subject P, and an acquisition area of "standard time" corresponding to legs of the subject P are set. In this case, as shown in FIG. 6B, the sensitivity-time products are different depending on acquisition areas. The sensitivity-time product at each top plate position is equal to the sum of the sensitivity-time products of two unit acquisition areas that contribute to the sensitivity-time product at each top plate position.

As the method for setting an acquisition time, a default value is predetermined for each of the levels, "short time", "standard time", and "long time". However, the present embodiment is not limited thereto. For example, a default value may be set only to one of the levels (for example, for "standard time"). In this case, the processing circuitry 73 sets the acquisition time of "short time" as a multiple of the acquisition time of "standard time" by a constant value (reduction of 10%), and sets the acquisition time of "long time" as a multiple of the acquisition time of "standard time" by a constant value (increase of 10%). The constant value for multiplication is automatically determined based on the entire acquisition time, the length of each acquisition area, and the level of acquisition time set to each acquisition area. In addition, the processing circuitry 73 may set a value obtained by subtracting a predetermined value (for example, one minute) from the acquisition time of "standard time" as the acquisition time of "short time", and set a value obtained by adding a predetermined value (for example, one minute) from the acquisition time of "standard time" as the acquisition time of "long time".

In the case where the overlap ratio between neighboring unit acquisition areas is fixed, the setting of the acquisition area is limited.

Figure 7:
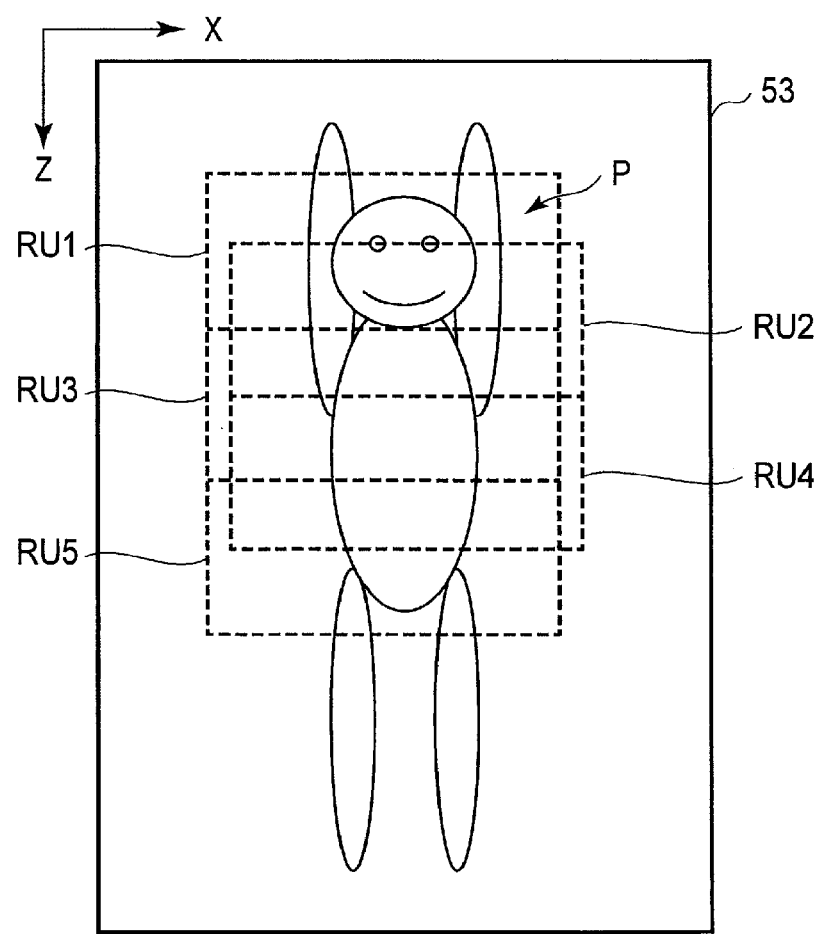
FIG. 7 is a schematic diagram showing unit acquisition areas when an overlap ratio rate is 50%, according to the first embodiment.

FIG. 7 is a schematic diagram showing unit acquisition area RUn (n is a number identifying a unit acquisition area) when an overlap ratio rate is 50%. In FIG. 7, the unit acquisition area RUn is shifted for each top plate stationary position in the X-axis direction for simplification, but the actual unit acquisition area is not shifted in the X-axis direction. As shown in FIG. 7, in the case where PET imaging is performed in a first unit acquisition area RU1, a second unit acquisition area RU2 is set to a position shifted by 50% in the Z-axis direction from the first unit acquisition area RU1. Namely, the length of the entire acquisition range can be set to be a multiple of a half of the length of the unit acquisition area RUn.

FIGS. 8A and 8B are schematic diagrams showing a limitation of setting acquisition areas in the case where the overlap ratio is fixed. The boundary of the acquisition areas is limited to match with the end of a unit acquisition area closest to the boundary in one of the acquisition areas defining the boundary or the end of a unit acquisition area closest to the boundary in another acquisition area. For example, in the case where position P1 is designated as the boundary of the acquisition area of "long time" and the acquisition area of "short time", the boundary is located at a non-end (a position other than the end) of a unit acquisition area closest to the boundary in the acquisition area of "long time" or a non-end of a unit acquisition area closest to the boundary in the acquisition area of "short time".

The processing circuitry 73 determines whether or not a position designated as a boundary is the end of a unit acquisition area closest to the boundary in one of the acquisition areas defining the boundary or the end of a unit acquisition area closest to the boundary in another acquisition area. The processing circuitry 73 determines that a boundary cannot be set to the designated position if the boundary corresponding to the designated position is not located at the end of the unit acquisition area. In this case, the processing circuitry 73 automatically sets a boundary to be an end P3 of a unit acquisition area placed at the end of the acquisition area of "long time" in which the position P1 is located, or an end P2 of a unit acquisition area placed at the end of the acquisition area of "short time".

The processing circuitry 73 according to the present embodiment uses VOL (Variable Overlap) to set an acquisition area at any position. Namely, the processing circuitry 73 determines whether or not a position designated as a boundary is the end of a unit acquisition area closest to the boundary in one of the acquisition areas defining the boundary, or the end of a unit acquisition area closest to the boundary in another acquisition area, and executes VOL if the boundary is not located at the end of the unit acquisition area.

FIGS. 9A and 9B are schematic diagrams showing the setting of acquisition areas using VOL. As shown in FIG. 9A, the overlap ratio is assumed to be 50% in the initial setting. Under this condition, it is assumed that the boundary of acquisition areas is designated at a position P1 which is a non-end of the unit acquisition area. If VOL is not used, the boundary is automatically set to be an end of one of the unit acquisition areas in which the designated position is located, for example, the end P2.

As shown in FIG. 9B, if VOL is used, the processing circuitry 73 automatically adjusts the overlap ratio to set the boundary at the designated position. Specifically, the processing circuitry 73 first identifies an acquisition area in which the designated position is located, based on a top plate position (a position in the Z-axis direction) of the designated position. In the case of FIG. 9A, since the position P1 is designated, the acquisition area of "short time" is identified. Next, the number of unit acquisition areas included in the identified acquisition area is determined. In FIG. 9A, the number of unit acquisition areas is five. Thereafter, a top plate position (a position in the Z-axis direction) of the designated position is identified. In FIG. 9A, if it is assumed that the length of each unit acquisition area is 10, a position of "28" from an end Ps of the entire acquisition range is identified. Next, the overlap ratio is calculated so that the end of the acquisition area is located at the designated position based on the number of unit acquisition areas. In FIG. 9B, the overlap ratio is 55%. The processing circuitry 73 applies the calculated overlap ratio to the acquisition area. Via this processing, the acquisition area can be set so that the boundary is set to be the designated position. The updated overlap ratio is displayed in the display region R2 shown in FIG. 4.

It has been explained that the overlap ratio in the acquisition area in which the designated position is located is changed; however, the present embodiment is not limited thereto. For example, the overlap ratio of an acquisition area adjacent to the acquisition area in which the designated position is located may be changed. For example, in the case of FIG. 9, the overlap ratio of the acquisition area of "long time" may be changed. In addition, the overlap ratio may be changed in both of the acquisition area in which the designated position is located and the adjacent acquisition area.

After step SA3, the processing circuitry 73 executes the imaging control function 733 (step SA4). In step SA4, the processing circuitry 73 synchronously controls the CT gantry 30 and the bed 50 to perform a CT positioning scan by the CT gantry 30. The CT positioning scan is CT imaging to acquire a whole body image of the subject P used for confirmation and setting, etc. of the imaging range. The CT positioning scan may be performed by a scano or a helical scan. The scano is accomplished by performing X-ray emission by the X-ray tube 31 and X-ray detection by the X-ray detector 32 while sliding the top plate 53 under the condition in which the rotation angle of the X-ray tube 31 and the X-ray detector 32 is fixed. The rotation angle of the X-ray tube 31 and the X-ray detector 32 is typically fixed to be aligned with the patient's frontal direction or the patient's lateral direction. The helical scan is accomplished by performing X-ray emission by the X-ray tube 31 and X-ray detection by the X-ray detector 32 while sliding the top plate 53 under the condition in which the X-ray tube 31 and the X-ray detector 32 are rotated in high-speed.

After step SA4, the processing circuitry 73 executes the reconstruction function 731 (step SA5). In step SA5, the processing circuitry 73 generates a CT positioning image based on the CT raw data acquired in step SA4.

After step SA5, the processing circuitry 73 executes the display control function 736 (step SA6). In step SA6, the processing circuitry 73 displays the CT positioning image generated in step SA5 as being inserted into the setting window displayed in step SA1. Namely, the subject model is replaced with the CT positioning image in the setting window. The acquisition areas set in step SA2 are superimposed on the CT positioning image. Via this processing, the user can confirm the positional relationship between the acquisition areas and the subject in more detail.

After step SA6, the processing circuitry 73 executes the acquisition area setting function 734 again (step SA7). In step SA7, the processing circuitry 73 performs fine adjustment of the acquisition areas set in step SA2, in response to a user's instruction through the input interface 76 input in the setting window displayed in step SA6. The acquisition areas are determined via the fine adjustment.

After step SA7, the processing circuitry 73 executes the imaging control function 733 (step SA8). In step SA8, the processing circuitry 73 synchronously controls the CT gantry 30 and the bed 50 to perform CT imaging by the CT gantry 30.

After step SA8, the processing circuitry 73 continuously executes the imaging control function 733 (step SA9). In step SA9, the processing circuitry 73 synchronously controls the PET gantry 10 and the bed 50 in accordance with the acquisition areas set in step SA2 or finely adjusted in step SA7, and the acquisition times set in step SA3, to perform step-and-shoot PET imaging by the PET gantry 10.

After step SA9, the processing circuitry 73 executes the reconstruction function 731 (step SA10). In step SA10, the processing circuitry 73 reconstructs a CT image based on the CT raw data acquired in step SA8, and reconstructs a PET image based on the coincidence event data acquired in step SA9. Specifically, the processing circuitry 73 reconstructs three-dimensional CT volume data based on the CT raw data, and performs rendering processing to the CT volume data to generate a two-dimensional display image. The CT image is a generic term of CT volume data and a display image based on the CT volume data. The processing circuitry 73 reconstructs three-dimensional PET volume data based on the coincidence event data, and performs rendering processing to the PET volume data to generate a two-dimensional display image. The PET image is a generic term of PET volume data and a display image based on the PET volume data.

After step SA10, the processing circuitry 73 executes the display control function 736 (step SA11). In step SA11, the processing circuitry 73 displays the CT image and the PET image reconstructed in step SA10 on the display 74.

The PET/CT examination according to the first embodiment is completed in the above processing.

The flow of the PET/CT examination shown in FIG. 3 is an example, and is not limited thereto. For example, the PET/CT examination shown in FIG. 3 includes both PET imaging and CT imaging; however, the present embodiment is not limited thereto, and may perform only PET imaging. In this case, step SA8 can be omitted. In addition, in the case where fine adjustment of the acquisition area is unnecessary, steps SA6 and SA7 can be omitted.

Steps SA2 to SA3 need not be performed. In this case, before setting an acquisition area and an acquisition time, a CT positioning scan is performed (step SA4), a CT positioning image is generated (step SA5), and a setting window in which the CT positioning image is inserted is displayed (step SA6). In the setting window, acquisition areas and acquisition times are set in a similar manner to steps SA2 and SA3. In this case, the user can set an acquisition area and an acquisition time by referring to the CT positioning image.

As stated above, the PET/CT apparatus 1 according to the first embodiment includes the bed 50, the display 74, and the processing circuitry 73. The bed 50 movably supports the top plate 53 in the long axis direction. The processing circuitry 73 displays the setting window for setting an acquisition time of PET event data for each acquisition area arranged in the long axis direction of the top plate 53 on the display 74. The processing circuitry 73 sets an acquisition time for each acquisition area in response to a setting instruction of the acquisition time for each acquisition area received via the setting window. The processing circuitry 73 performs PET imaging for each acquisition area in accordance with the set acquisition time while intermittently moving the top plate 53 in the long axis direction, and acquires PET event data that represents the count of gamma rays emitted from the subject P. The processing circuitry 73 generates a PET image based on the acquired PET event data.

With the above configuration, the PET/CT apparatus 1 according to the first embodiment that sets the acquisition time for each acquisition area can easily set the acquisition areas and the acquisition times.

Application Example 1

In the case where the difference in acquisition time between two neighboring acquisition areas (acquisition time difference) is large, the image quality between the two neighboring acquisition areas is greatly changed. This may cause difficulty in image observation.

The processing circuitry 73 according to the application example 1 executes the image processing function 732 if the difference in acquisition time between two neighboring acquisition areas is greater than a threshold value, and performs image filtering to the PET volume data to suppress the change in the image quality between the two neighboring acquisition areas.

Specifically, the processing circuitry 73 calculates the difference between the acquisition times set in two neighboring acquisition areas, and compares the calculated difference with the threshold value. The threshold value is set to be an acquisition time difference that causes the gap in image quality that is not allowable to the user. For example, the threshold value may be set as a value equal to the difference between the acquisition time of "short time" and the acquisition time of "long time". If the acquisition time difference is smaller than the threshold value, the processing circuitry 73 does not perform image filtering.

If the acquisition time difference is greater than the threshold value, the processing circuitry 73 selects image filtering to be applied. Various types of image filtering can be selected to be applied, and any types of image filtering that has a smoothing effect to the pixel values of the PET volume data may be applied. For example, a smoothing filter, a Gauss filter, a median filter, a low-pass filter, etc. can be applied as the image filtering. The filtering to adjust the linearity in the Z-axis direction may be a linear filter or a non-linear filter. The image filtering may be discretionarily selected by the user through the input interface 76, or automatically selected. The filter strength for smoothing can be discretionarily set. If the image filtering is selected, the processing circuitry 73 applies the selected image filtering to the PET volume data in the Z-axis direction. Via this processing, the gap in image quality caused by the acquisition time difference between the neighboring acquisition areas can be suppressed.

Figure 10:
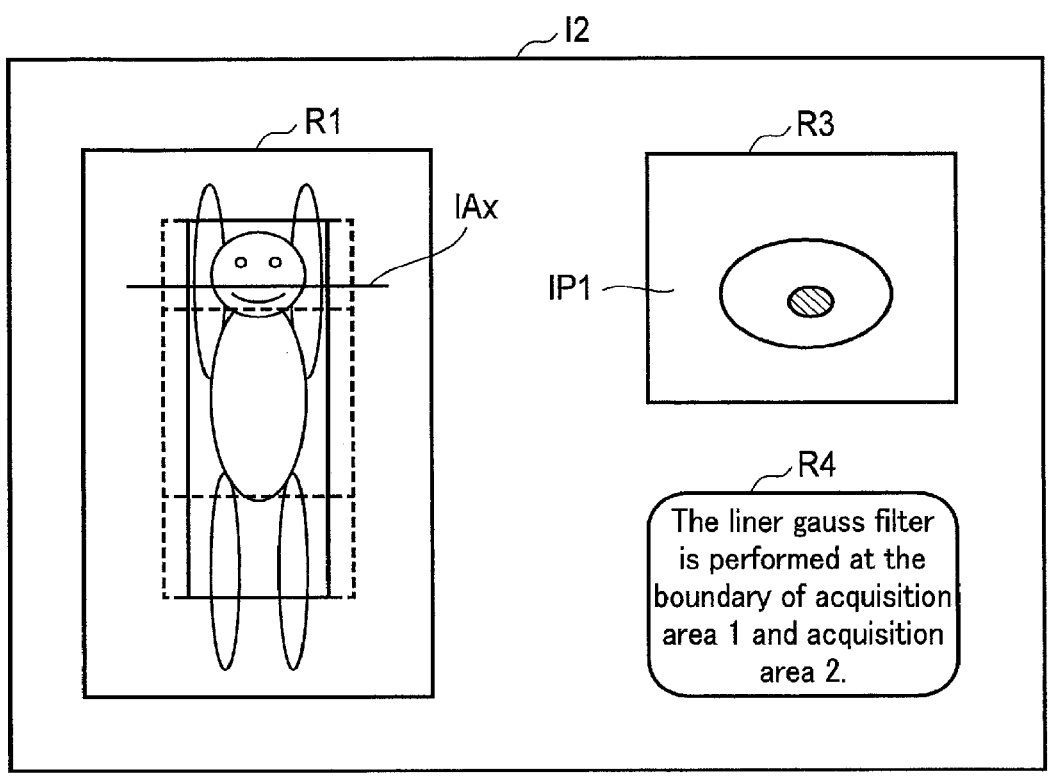
FIG. 10 is a diagram showing an example of a display window of an image according to application example 1.

FIG. 10 is a diagram showing an example of a display window 12 of an image according to application example 1. As shown in FIG. 10, the subject model PM in which the acquisition areas are superimposed is displayed in the display region R1 of the display window 12. An indicator IAx indicating a position of axial cross section of a display target is displayed on the subject model PM. A PET/CT image IP1 of the axial cross section corresponding to the indicator IAx is displayed in a display region R3. Information related to the image filtering applied to the PET volume data is displayed in a display region R4. Information related to the image filtering applied to the PET volume data may be, for example, information indicating that image filtering is applied, the type and the strength of the applied image filtering, and the top plate position (a position in the Z-axis direction) at which the image filtering is applied. For example, as shown in FIG. 10, the information may be "The liner Gauss filter is performed to the boundary of acquisition area 1 and acquisition area 2", etc. As stated above, by displaying the information of the applied image filtering, the user can recognize the fact that the image filtering is applied, the type of the applied image filtering, and the part in which the image filtering is applied.

Application Example 2

In the application example 1, if the difference in acquisition time between two neighboring acquisition areas is significant, the image filtering is performed to the PET volume data. However, the present embodiment is not limited thereto. The processing circuitry 73 according to the application example 2 adjusts the acquisition time of the boundary portion between two neighboring acquisition areas to suppress the difference in acquisition time between the two neighboring acquisition areas. According to the application example 2, the boundary portion is typically defined by at least one of the unit acquisition area at the end of a first acquisition area (specifically, the end close to a second acquisition area side) among two neighboring acquisition areas, and the unit acquisition area at the end of a second acquisition area (specifically, the end close to the first acquisition area side) among two neighboring acquisition areas.

Figure 11A:
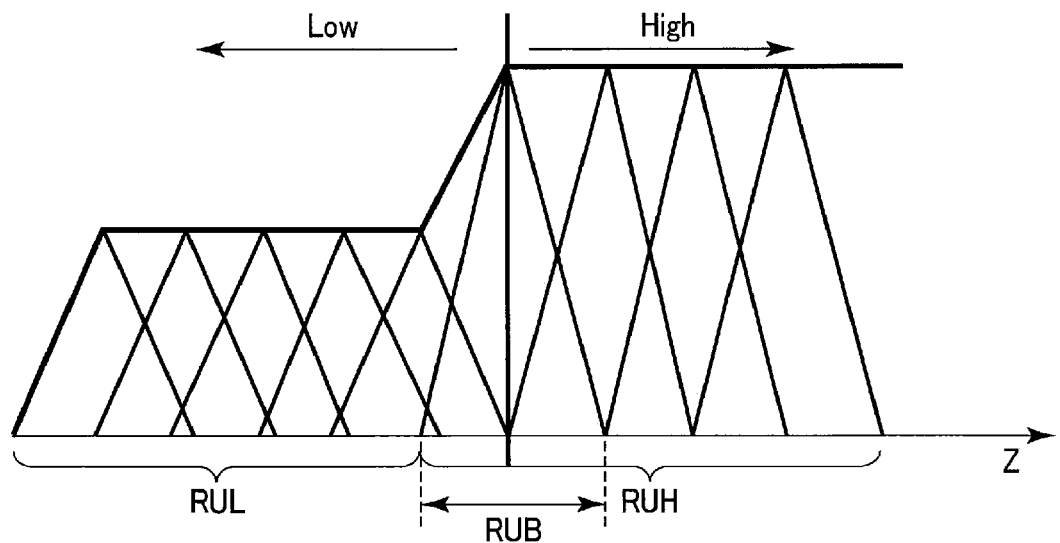
FIGS. 11A and 11B are schematic diagrams showing adjustment process of acquisition times at a boundary portion of acquisition areas according to application example 2.
Figure 11B:
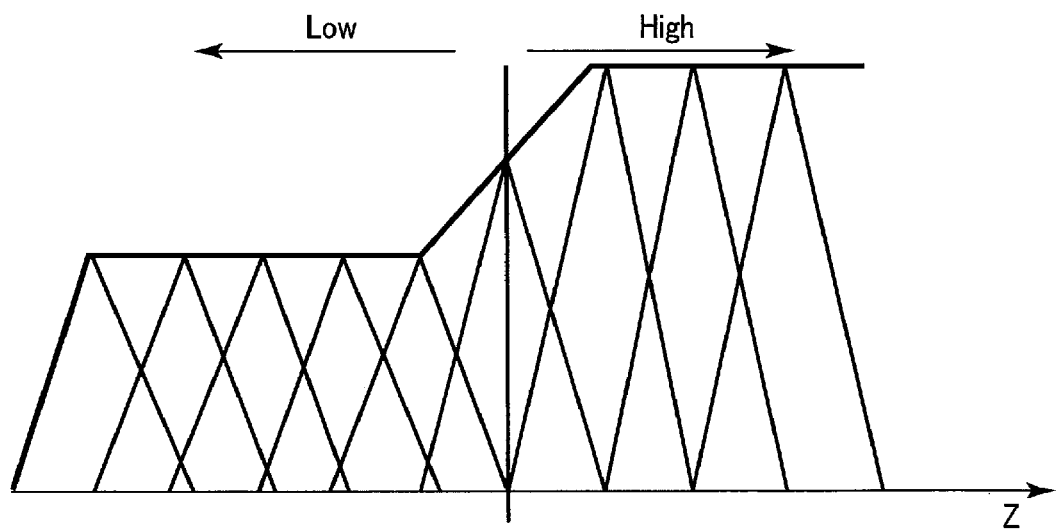

FIGS. 11A and 11B are schematic diagrams showing adjustment process of acquisition times at a boundary portion RUB of acquisition areas according to application example 2. As shown in FIG. 11A, an acquisition area RUL of the acquisition time, "short time", is adjacent to an acquisition area RUH of the acquisition time, "long time". In this case, as shown in FIG. 11B, an acquisition time between the acquisition time of "short time" and the acquisition time of "long time" is set to the boundary portion RUB between the acquisition area RUL of "short time" and the acquisition area RUH of "long time".

Specifically, the processing circuitry 73 first identifies the boundary portion RUB between the acquisition area RUL of "short time" and the acquisition area RUH of "long time". The boundary portion RUB is, for example, set to be a unit acquisition area which is adjacent to the acquisition area of "short time" among the unit acquisition areas in the acquisition area RUH of "long time". Next, the processing circuitry 73 sets an acquisition time of the boundary portion RUB to be an intermediate value of the acquisition times allocated to two unit acquisition areas bracketing the boundary portion RUB. For example, in the case of FIG. 11B, an acquisition time between the acquisition time, "short time", of the unit acquisition area adjacent to the boundary portion RUB in the negative Z-axis direction and the acquisition time, "long time", of the unit acquisition area adjacent to the boundary portion RUB in the positive Z-axis direction, for example, a "standard time", is set to the boundary portion RUB.

Via this processing, the acquisition area difference between the acquisition areas bracketing the boundary portion is suppressed, thereby mitigating the gap in image quality. In the above example, the boundary portion may, for example, be set to be a unit acquisition area which is adjacent to the acquisition area RUH of "long time" among the unit acquisition areas in the acquisition area RUL of "short time". In addition, the boundary portion may, for example, be set to be both of a unit acquisition area which is adjacent to the acquisition area RUL, "short time", among the unit acquisition areas in the acquisition area RUH of "long time", and a unit acquisition area which is adjacent to the acquisition area RUH, "long time", among the unit acquisition areas in the acquisition area RUL of "short time". The boundary portion may include not only a unit acquisition area of the unit acquisition areas in an acquisition area, which is the closest to an adjacent acquisition area, but also a unit acquisition area which is the second closest to the adjacent acquisition area, a unit acquisition area which is the third closest to the adjacent acquisition area, etc.

In the above example, the acquisition time of the boundary portion between the acquisition area of the acquisition time, "short time", and the acquisition area of the acquisition time, "long time" is adjusted; however, the present embodiment is not limited thereto. For example, the acquisition time of the boundary portion between the acquisition area of the acquisition time, "short time" and the acquisition area of the acquisition time, "standard time", or the acquisition time of the boundary of between the acquisition area of the acquisition time, "standard time" and the acquisition area of the acquisition time, "long time" may be adjusted. In this case, the acquisition time of the boundary portion is respectively set to be an intermediate time between the acquisition time, "short time" and the acquisition time, "standard time", or an intermediate time between the acquisition time, "standard time" and the acquisition time, "long time".

The acquisition time of the boundary portion is assumed to be set as an intermediate time of the acquisition times of acquisition areas bracketing the boundary portion; however, the present embodiment is not limited thereto. For example, the acquisition time of the boundary portion may be set non-linearly in accordance with the top plate position (a position in the Z-axis direction).

Second Embodiment

The PET/CT apparatus 1 according to the second embodiment automatically sets an acquisition area and an acquisition time based on a CT positioning image. The PET/CT apparatus 1 according to the second embodiments will be described. In the explanation below, structural elements having substantially the same functions as in the first embodiment will be denoted by the same reference symbols, and a repetitive description will be given only where necessary.

Figure 12:
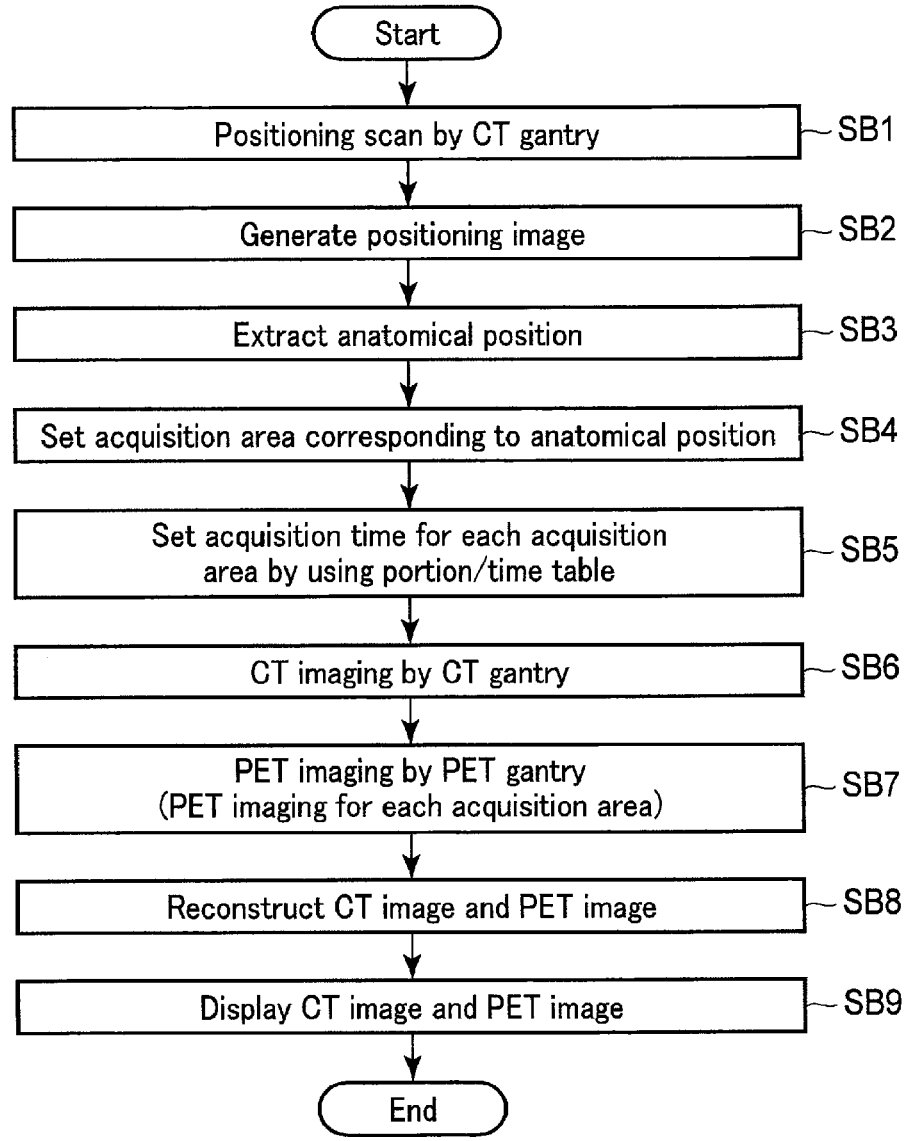
FIG. 12 is a flowchart of a typical PET/CT examination by the PET/CT apparatus according to the second embodiment.

FIG. 12 is a flowchart of a typical PET/CT examination by the PET/CT apparatus 1 according to the second embodiment.

As shown in FIG. 12, the processing circuitry 73 executes the imaging control function 733 (step SB1). In step SB1, the processing circuitry 73 synchronously controls the CT gantry 30 and the bed 50 to perform a positioning scan by the CT gantry 30.

After step SB1, the processing circuitry 73 executes the reconstruction function 731 (step SB2). In step SB2, the processing circuitry 73 generates a positioning image related to the subject, based on the CT raw data acquired in step SB1.

After step SB2, the processing circuitry 73 executes the image processing function 732 (step SB3). In step SB3, the processing circuitry 73 extracts an anatomical position of the subject from the positioning image via image processing. Any method can be applied to extract an anatomical position. The processing circuitry 73 extracts an anatomical position by using a known method such as the threshold processing, the region growing processing, image recognition processing, etc. An anatomical position to be extracted is preferably an organ such as a heart, liver, bladder, brain, etc.

After step SB3, the processing circuitry 73 executes the acquisition area setting function 734 (step SB4). In step SB4, the processing circuitry 73 sets an acquisition area corresponding to the anatomical position extracted in step SB3. Specifically, the processing circuitry 73 sets a local area that includes the extracted anatomical position as an acquisition area. The acquisition area may be set to be an area that includes the extracted anatomical position and a margin area relative to the Z-axis direction. The margin area may preferably be set for each anatomical position in advance.

After step SB4, the processing circuitry 73 executes the acquisition time setting function 735 (step SB5). In step SB5, the processing circuitry 73 sets an acquisition time for each acquisition area set in step SB4, by using a portion/time table.

FIG. 13 illustrates an example of a portion/time table. As shown in FIG. 13, the portion/time table is an LUT (Look Up Table) in which anatomical positions are associated with respective acquisition times. The suitable acquisition time is associated with each anatomical position in the portion/time table. The combinations of an anatomical position and an acquisition time are set by the user through the input interface 76. For example, the acquisition time for an anatomical position, "brain", is set to be "30 seconds". The portion/time table is stored, for example, in the memory 75. The portion/time table is assumed to be an LUT; however, the present embodiment is not limited thereto. A database, etc. that is capable of storing the relationships between anatomical positions and acquisition times may be adopted.

After step SB5, the processing circuitry 73 executes the imaging control function 733 (step SB6). In step SB6, the processing circuitry 73 synchronously controls the CT gantry 30 and the bed 50 to perform CT imaging by the CT gantry 30.

After step SB6, the processing circuitry 73 continuously executes the imaging control function 733 (step SB7). In step SB7, the processing circuitry 73 synchronously controls the PET gantry 10 and the bed 50 to perform step-and-shoot PET imaging by the PET gantry 10.

After step SB7, the processing circuitry 73 executes the reconstruction function 731 (step SB8). In step SB8, the processing circuitry 73 reconstructs a CT image based on the CT raw data acquired in step SB6, and reconstructs a PET image based on the coincidence event data acquired in step SB7.

After step SB8, the processing circuitry 73 executes the display control function 736 (step SB9). In step SB9, the processing circuitry 73 displays the CT image and the PET image reconstructed in step SB8 on the display 74.

The PET/CT examination according to the second embodiment is completed in the above processing.

The flow of the PET/CT examination according to the second embodiment shown in FIG. 12 is an example, and is not limited thereto. If, for example, in step SB3 the processing circuitry 73 can extract an anatomical position from the CT raw data acquired in step SB1, it is not necessary to generate a positioning image in step SB2.

As stated above, the PET/CT apparatus 1 according to the second embodiment includes the bed 50, the PET gantry 10, the CT gantry 30, and the processing circuitry 73. The bed 50 movably supports the top plate 53 in the long axis direction. The PET gantry 10 performs PET imaging. The CT gantry 30 performs CT imaging. The processing circuitry 73 performs a positioning scan by the CT gantry 30 and acquires CT raw data. The processing circuitry 73 sets an acquisition time for an acquisition area for each portion of the subject P for an intermittent movement scan by the PET gantry 10, using the acquired CT raw data or the positioning image based on the CT raw data.

With the above configuration, the acquisition time of the acquisition area for each position of the subject P can be automatically set based on the CT raw data acquired by performing the positioning scan by the CT gantry 30, or the positioning image. Accordingly, the acquisition time for each acquisition area can be easily set.

Third Embodiment

The PET/CT apparatus 1 according to the third embodiment automatically sets an acquisition area and an acquisition time based on a PET positioning image. The PET/CT apparatus 1 according to the third embodiment will be described. In the explanation below, structural elements having substantially the same functions as in the first embodiment will be denoted by the same reference symbols, and a repetitive description will be given only where necessary.

FIG. 14 is a flowchart of a typical PET/CT examination by the PET/CT apparatus 1 according to the third embodiment.

As shown in FIG. 14, the processing circuitry 73 first executes the imaging control function 733 (step SC1). In step SC1, the processing circuitry 73 synchronously controls the PET gantry 10, the CT gantry 30, and the bed 50 to concurrently perform a positioning scan by the CT gantry 30 and a positioning scan by the PET gantry 10. Specifically, the processing circuitry 73 performs a CT positioning scan by the CT gantry 30 while sliding the top plate 53 in the positive Z-axis direction, and thereafter, performs a PET positioning scan by the PET gantry 10 while continuously sliding the top plate 53 in the positive Z-axis direction. In the positioning scan by the PET gantry 10, the processing circuitry 73 records the count of single event data or the coincidence event data for each Z-axis direction position of the top plate 53. Since the smaller count of PET event data is sufficient for the positioning scan in comparison with the PET imaging, it is not necessary to stop the top plate 53 while acquiring PET event data.

After step SC1, the processing circuitry 73 executes the reconstruction function 731 (step SC2). In step SC2, the processing circuitry 73 generates a CT positioning image related to the subject, based on the CT raw data acquired in step SC1, and generates a PET positioning image related to the subject, based on the PET event data acquired in step SC1.

After step SC2, the processing circuitry 73 executes the image processing function 732 (step SC3). In step SC3, the processing circuitry 73 extracts an anatomical position of the subject from the PET positioning image via image processing. For example, the count of PET event data for a brain or a bladder tends to be greater than that for other portions. Accordingly, the processing circuitry 73 performs threshold processing to the PET positioning image, extracts an image area with the count equal to or greater than a threshold, sets an image area positioned at the head side as a brain area, and sets an image area positioned at the leg side as a bladder area. Thereafter, the processing circuitry 73 extracts anatomical positions of the subject P from the PET positioning image based on the distance between the brain area and the bladder area (hereinafter referred to as brain-to-bladder distance). For example, an image area with the relatively greater count is extracted from the positioning image, the distance between the extracted image area and the brain area (hereinafter referred to as brain-to-target distance) and the distance between the extracted image area and the bladder area (hereinafter referred to as bladder-to-target distance) are calculated, and an anatomical position of the extracted image area is identified based on the brain-to-target distance, the bladder-to-target distance, the brain-to-bladder distance, and empirical positional information of the anatomical positions.

After step SC3, the processing circuitry 73 executes the acquisition area setting function 734 (step SC4). In step SC4, the processing circuitry 73 sets an acquisition area corresponding to each anatomical position extracted in step SC3. The processing in step SC4 is similar to that in step SB4. After step SC4, the processing circuitry 73 executes the acquisition time setting function 735 (step SC5). In step SC5, the processing circuitry 73 sets an acquisition time for each acquisition area set in step SC4, by using the portion/time table. The processing in step SC5 is similar to that in step SB5.

After step SC5, the processing circuitry 73 executes the imaging control function 733 (step SC6). In step SC6, the processing circuitry 73 synchronously controls the CT gantry 30 and the bed 50 to perform CT imaging by the CT gantry 30.

After step SC6, the processing circuitry 73 continuously executes the imaging control function 733 (step SC7). In step SC7, the processing circuitry 73 synchronously controls the PET gantry 10 and the bed 50 to perform step-and-shoot PET imaging by the PET gantry 10.

After step SC7, the processing circuitry 73 executes the reconstruction function 731 (step SC8). In step SC8, the processing circuitry 73 reconstructs a CT image based on the CT raw data acquired in step SC6, and reconstructs a PET image based on the coincidence event data acquired in step SC7.

After step SC8, the processing circuitry 73 executes the display control function 736 (step SC9). In step SC9, the processing circuitry 73 displays the CT image and the PET image reconstructed in step SC8 on the display 74.

The PET/CT examination according to the third embodiment is completed in the above processing.

The flow of the PET/CT examination according to the third embodiment shown in FIG. 14 is an example, and is not limited thereto. For example, if in step SC3 the processing circuitry 73 can extract an anatomical position from the PET event data acquired in step SC1, it is not necessary to generate a PET positioning image in step SC2. For example, the processing circuitry 73 records the count of single event data or the coincidence event data for each top plate position (or each unit acquisition area) in the PET positioning scan. The processing circuitry 73 may estimate an anatomical position based on the recorded count. For example, in the case for the whole body scan using FDG (fluorodeoxyglucose), the portions with the high count are a brain and a bladder. The processing circuitry 73 estimates each anatomical position (organ) in the subject's body, based on the brain-to-bladder distance. Specifically, the processing circuitry 73 first plots the count in the body axis direction. The FDG accumulation is intense and the count is high in the brain, heart, and bladder. The processing circuitry 73 pre-stores the FDG accumulation tendency for each anatomical position. The processing circuitry 73 identifies a position of the brain, heart, and bladder based on the accumulation tendency and the distribution of count relative to the body axis direction. The processing circuitry 73 estimates positions of other organs based on the relative positional relationships between the brain, heat, and bladder and the organs. In the case where the first peak of counts appears at Z=10 cm, the second peak of counts appears at Z=40 cm, and the third peak of counts appears at Z=90 cm, it is estimated that the position where Z=10 cm is the brain, the position where Z=40 cm is the heart, and the position where Z=90 cm is the bladder. The processing circuitry 73 estimates positions of other organs based on the relative positional relationships between the brain, the bladder, and the organs.

In step SC5, the processing circuitry 73 is assumed to set an acquisition time for each acquisition area by using the portion/time table. However, the present embodiment is not limited thereto. For example, the processing circuitry 73 may calculate an acquisition time for acquisition areas corresponding to respective anatomical positions in accordance with the entire acquisition time of the PET imaging and the count for respective anatomical positions. Specifically, the processing circuitry 73 proportionally divides the entire acquisition time of the PET imaging in accordance with the number of acquisition areas, and calculates an initial value of acquisition time for each acquisition area. Next, the processing circuitry 73 determines a weight to be multiplied by the initial value in accordance with the count for an anatomical position corresponding to each acquisition area. The weight is determined so that the acquisition time reduces as the count becomes greater, and the acquisition time increases as the count becomes smaller. The processing circuitry 73 determines a final acquisition time by multiplying the initial value by the weight for each acquisition area. By determining the acquisition time for each acquisition area without using the portion/time table, it is possible to set an acquisition time in accordance with the actual condition of the subject.

As stated above, the PET/CT apparatus 1 according to the third embodiment includes the bed 50, the PET gantry 10, the CT gantry 30, and the processing circuitry 73. The bed 50 movably supports the top plate 53 in the long axis direction. The PET gantry 10 performs PET imaging. The CT gantry 30 performs CT imaging. The processing circuitry 73 performs a positioning scan by the PET gantry 30 and acquires PET event data. The processing circuitry 73 sets an acquisition time for an acquisition area for each portion of the subject P for an intermittent movement scan by the PET gantry 10, using the acquired PET event data or the positioning image based on the PET event data.

With the above configuration, the acquisition time of the acquisition area for each position of the subject P can be automatically set based on the PET event data acquired by performing the positioning scan by the PET gantry 30, or the positioning image. Accordingly, the acquisition time for each acquisition area can be easily set.

Fourth Embodiment

The PET/CT apparatus 1 according to the fourth embodiment automatically sets an acquisition area and an acquisition time based on a PET positioning image. The PET/CT apparatus 1 according to the fourth embodiments will be described. In the explanation below, structural elements having substantially the same functions as in the first embodiment will be denoted by the same reference symbols, and a repetitive description will be given only where necessary.

Figure 15:
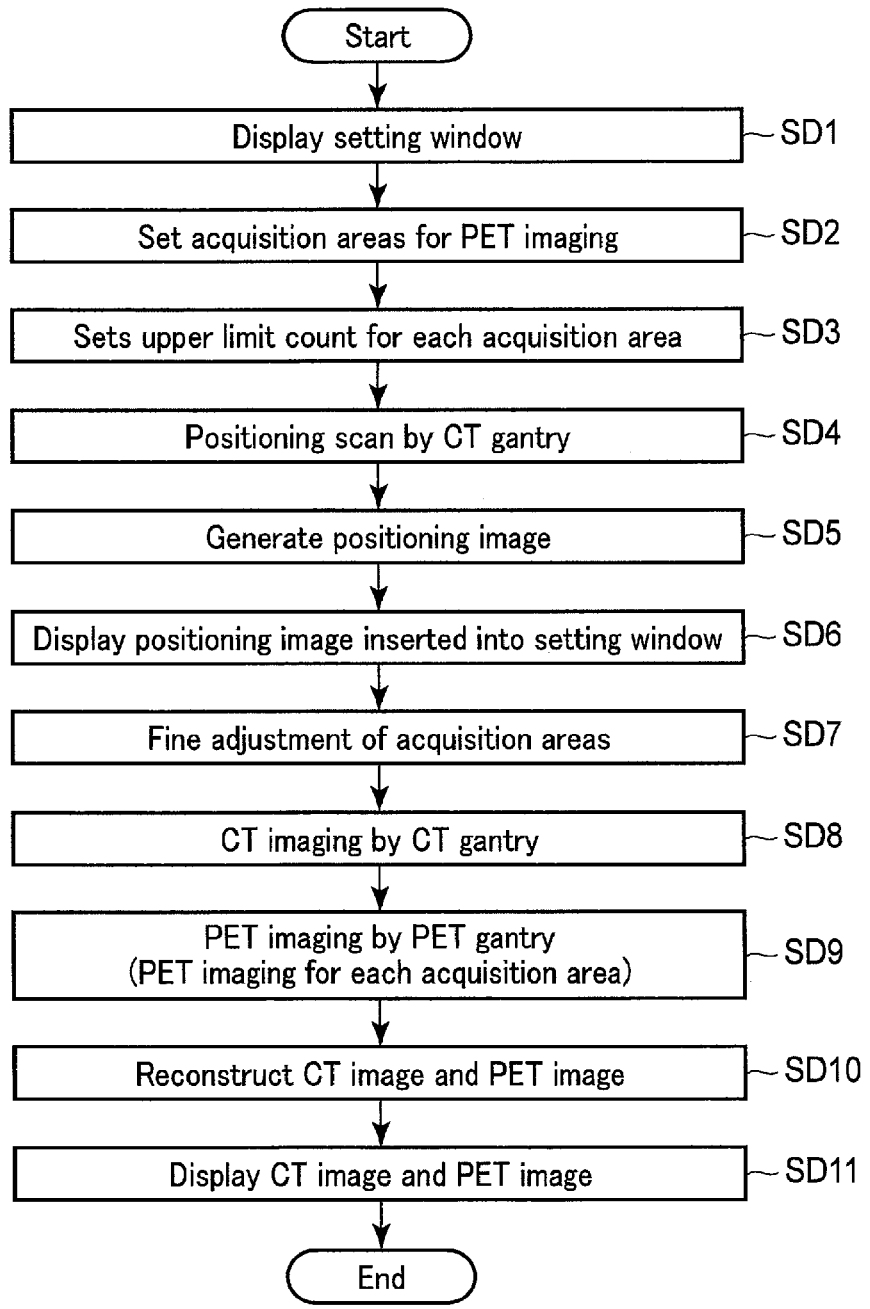
FIG. 15 is a flowchart of a typical PET/CT examination by the PET/CT apparatus according to the fourth embodiment.

FIG. 15 is a flowchart of a typical PET/CT examination by the PET/CT apparatus 1 according to the fourth embodiment.

As shown in FIG. 15, the processing circuitry 73 first executes the display control function 736 (step SD1). In step SD1, the processing circuitry 73 displays a setting window on the display 74 as a user interface through which an acquisition area and an acquisition time for the step-and-shoot PET imaging are set. The processing in step SD1 is similar to that in step SA1.

After step SD1, the processing circuitry 73 executes the acquisition area setting function 734 (step SD2). In step SD2, the processing circuitry 73 sets an acquisition area for the PET imaging in response to a user's instruction through the input interface 76 input in the setting window displayed in step SD1. The processing in step SD2 is similar to that in step SA2.

After step SD2, the processing circuitry 73 executes the acquisition time setting function 735 (step SD3). In step SD3, the processing circuitry 73 sets an upper limit value of the count (hereinafter referred to as an upper limit count) for each acquisition area set in step SD2. The processing in step SD3 is similar to that in step SA3. In step SD3, the upper limit count is set instead of the acquisition time. Similar to the acquisition time, the upper limit count includes multiple levels, for example, three levels, and the user discretionarily sets the upper limit count among the multiple levels by a setting instruction input through the input interface. The set upper limit count and acquisition areas are stored in the memory 75, etc., the upper limit count being associated with the corresponding acquisition area.

After step SD3, the processing circuitry 73 executes the imaging control function 733 (step SD4). In step SD4, the processing circuitry 73 synchronously controls the CT gantry 30 and the bed 50 to perform a positioning scan by the CT gantry 30.

After step SD4, the processing circuitry 73 executes the reconstruction function 731 (step SD5). In step SD5, the processing circuitry 73 generates a CT positioning image based on the CT raw data acquired in step SD4.

After step SD5, the processing circuitry 73 executes the display control function 736 (step SD6). In step SD6, the processing circuitry 73 displays the CT positioning image generated in step SD5 as being inserted into the setting window. Namely, the subject model is replaced with the CT positioning image in the setting window. The acquisition areas set in step SD2 are superimposed on the CT positioning image. Via this processing, the user can confirm the positional relationship between the acquisition areas and the subject P in more detail.

After step SD6, the processing circuitry 73 executes the acquisition area setting function 734 again (step SD7). In step SD7, the processing circuitry 73 performs fine adjustment of the acquisition areas set in step SD2, in response to a user's instruction through the input interface 76 input in the setting window displayed in step SD6.

After step SD7, the processing circuitry 73 executes the imaging control function 733 (step SD8). In step SD8, the processing circuitry 73 synchronously controls the CT gantry 30 and the bed 50 to perform CT imaging by the CT gantry 30.

After step SD8, the processing circuitry 73 continuously executes the imaging control function 733 (step SD9). In step SD9, the processing circuitry 73 synchronously controls the PET gantry 10 and the bed 50 to perform step-and-shoot PET imaging by the PET gantry 10.

FIG. 16 is a flowchart of a typical PET imaging with step-and-shoot acquisition performed in step SD9 of FIG. 15, according to the fourth embodiment. As shown in FIG. 16, the processing circuitry 73 controls the bed 50 to move the top plate 53 to the initial (first) unit acquisition area of the PET imaging (step S101).

After step S101, the processing circuitry 73 identifies the upper limit count of the first unit acquisition area (step S102). Specifically, an acquisition area in which the first unit acquisition area is included is identified, and the upper limit count set to the identified acquisition area is determined. Step S102 is typically performed while moving the top plate 53.

After step S102, the gamma ray detectors 17 detect annihilation gamma rays emitted from the subject P (step S103). The signal processing circuitry 13 generates single event data of the detected gamma rays, and the coincidence circuitry 15 generates coincidence event data.

After step S103, the processing circuitry 73 waits until the number of coincidence events reaches the upper limit count (step S104). Specifically, the processing circuitry 73 compares the number of coincidence events with the upper limit count, and determines whether or not the number of coincidence events reaches the upper limit count. If it is determined that the number of coincidence events does not reach the upper limit count (step S104: No), the processing circuitry 73 repeats steps S103 and S104.

If it is determined that the number of coincidence events reaches the upper limit count (step S104: Yes), the processing circuitry 73 determines whether or not to terminate the PET imaging (step S105). Specifically, the processing circuitry 73 determines whether or not the current unit acquisition area is the last unit acquisition area. If it is determined that the current unit acquisition area is not the last unit acquisition area (step S105: No), the processing circuitry 73 controls the bed 50 to move the top plate 53 to the next unit acquisition area (step S106). Thereafter, identification of the upper limit count (step S102), detection of gamma rays (step S103), determination of whether or not the count reaches the upper limit count (step S104), and determination of whether or not to terminate the PET imaging (step S105) are performed for the next unit acquisition area.

If it is determined that the current unit acquisition area is the last unit acquisition area (step S105: Yes), the processing circuitry 73 terminates the step-and-shoot PET imaging by the PET gantry 10 (step SD9).

After step SD9, the processing circuitry 73 executes the reconstruction function 731 (step SD10). In SD10, the processing circuitry 73 reconstructs a CT image based on the CT raw data acquired in step SD8, and reconstructs a PET image based on the coincidence event data acquired in step SD9.

After step SD10, the processing circuitry 73 executes the display control function 736 (step SD11). In step SD11, the processing circuitry 73 displays the CT image and the PET image reconstructed in step SD10 on the display 74.

The PET/CT examination according to the fourth embodiment is completed in the above processing.

The flow of the PET/CT examination shown in FIG. 15 is an example, and is not limited thereto. For example, the PET/CT examination shown in FIG. 15 includes both PET imaging and CT imaging; however, the present embodiment is not limited thereto, and may perform only PET imaging. In this case, step SD8 can be omitted. In addition, in the case where fine adjustment of the acquisition area is unnecessary, steps SD6 and SD7 can be omitted.

The processing circuitry 73 is assumed to set the acquisition area and the upper limit count in response to the user's instruction through the setting window. However, the present embodiment is not limited thereto. Namely, the processing circuitry 73 may extract an anatomical position from the CT raw data acquired by the CT positioning scan or the CT positioning image, set the acquisition area corresponding to the anatomical position, and automatically set the upper limit count corresponding to the acquisition area, as in the second embodiment. The anatomical position may be extracted from the PET event data acquired by the PET positioning scan or the PET positioning image, as in the third embodiment. The method of automatically setting the upper limit count may adopt the position/count table in which the upper limit count is associated with each anatomical position. The processing circuitry 73 identifies the upper limit count associated in the position/count table for an anatomical position included in each acquisition area, and sets the identified upper limit count as the upper limit count of each acquisition area. Via this processing, the acquisition area and the upper limit count can be set without receiving the user's instructions.

As stated above, the PET/CT apparatus 1 according to the fourth embodiment includes the memory 75, the bed 50, and the processing circuitry 73. The memory 75 stores the upper limit value (upper limit count) for each portion of the subject P. The bed 50 movably supports the top plate 53 in the long axis direction. The processing circuitry 73 acquires count data indicating the count of the gamma rays emitted from the body of the subject P placed on the top plate 53. The processing circuitry 73 controls the bed 50 to intermittently move the top plate 53 in the long axis direction, in order to perform the PET imaging on the subject P. In this case, the processing circuitry 73 moves the top plate 53 to the next position if the count reaches the upper limit count corresponding to the image target portion.

With the above configuration, the processing circuitry 73 moves the top plate 53 to the next position if the count reaches the upper limit count in the step-and-shoot PET imaging. According to the fourth embodiment, the acquisition time for each portion is indirectly set and controlled by setting the upper limit count for each portion.

According to at least one or more embodiments, the acquisition time for each portion can be easily set in the PET imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
    a bed that movably supports a top plate in a long axis direction;
    a display that displays a setting window through which an acquisition time of PET event data is set for each of acquisition areas arranged in the long axis direction of the top plate; and
    processing circuitry that:
        sets an acquisition time for each of the acquisition areas in response to a setting instruction of the acquisition time for each of the acquisition areas received through the setting window;
        performs PET imaging for each of the acquisition areas in accordance with the set acquisition time, and acquires PET event data that represents the count of gamma rays emitted from a subject, and
        generates a PET image based on the acquired PET event data,
    wherein the acquisition areas each include a unit acquisition area or a plurality of unit acquisition areas which overlap with each other in the long axis direction with a variable overlap ratio,
    each of the unit acquisition areas corresponds to a coverage of a gamma ray detector included in a PET gantry, and
    the processing circuitry sets the plurality of acquisition areas arranged in the long axis direction and the acquisition time for each of the acquisition areas, and
    when a user designates a given position of the set acquisition areas, the processing circuitry adjusts the overlap ratio of a first acquisition area set with a first acquisition time and including the given position of the acquisition areas or a second acquisition area adjacent to the first acquisition area and having a second acquisition time different than the first acquisition time so that a boundary between the first area and the second area matches the given position.

2. The medical image diagnostic apparatus according to claim 1, wherein:
    the processing circuitry sets, as an acquisition time, a level designated from among predetermined levels through an input device for each of the acquisition areas.

3. The medical image diagnostic apparatus according to claim 2, wherein:
    a value of each of the levels is independently set, or is set by multiplying a value of a level by a constant value.

4. The medical image diagnostic apparatus according to claim 1, wherein:

the display displays an indicator of each of the acquisition areas included in the setting window in a color corresponding to the respective set acquisition times.

5. The medical image diagnostic apparatus according to claim 1, wherein:
the processing circuitry adjusts an acquisition time of an overlap portion between the two neighboring acquisition areas to decrease a gap in acquisition time between the two neighboring acquisition areas.

6. The medical image diagnostic apparatus according to claim 1, wherein:
the processing circuitry determines division of the acquisition areas and sets the acquisition times, thereafter the processing circuitry performs a positioning scan on the subject to acquire scan data, and generates a positioning image for the subject based on the scan data; and
the display displays the positioning image on the setting window, and displays the acquisition areas superimposed on the positioning image to adjust the division of the acquisition areas.

7. The medical image diagnostic apparatus according to claim 1, wherein:
the processing circuitry performs filtering to the PET image, and reduces a gap in image quality between two neighboring acquisition areas which are different in acquisition time.

8. A medical image diagnostic apparatus comprising:
a bed that movably supports a top plate in a long axis direction;
a PET gantry that performs PET imaging;
a CT gantry that performs CT imaging;
processing circuitry that:
performs a positioning scan on a subject placed on the top plate by the PET gantry, while moving the top plate in the long axis direction, to acquire PET event data; and
sets an acquisition time for each of acquisition areas for an intermittent movement scan that performs the PET imaging to each of the acquisition areas by the PET gantry while intermittently moving the top plate in the long axis direction, based on the PET event data or a positioning image based on the PET event data,
wherein the processing circuitry extracts a brain area and a bladder area of the subject based on counts of the acquired PET event data, extracts each of the portions of the subject based on a distance between the brain and the bladder, identifies a count each of portions of the subject based on the acquired PET event data, and sets an acquisition area corresponding to respective portions of the subject and sets an acquisition time for each of the acquisition areas corresponding to respective portions of the subject in accordance with the count of the PET event data corresponding to said respective portions of the subject.

9. A medical image diagnostic apparatus comprising:
a memory that stores an upper limit value of the count for each of portions of a subject;
a bed that movably supports a top plate in a long axis direction; and
processing circuitry that:
acquires count data that indicates a count of gamma rays emitted from respective portions of a body of the subject placed on the top plate,
sets an acquisition area corresponding to respective portions of the subject and sets an acquisition time for each of the acquisition areas corresponding to respective portions of the subject in accordance with the count data corresponding to said respective portions of the subject, and
controls the bed to intermittently move the top plate in the long axis direction in order to perform PET imaging on the subject, wherein the processing circuitry moves the top plate to a next position if the count reaches the upper limit value corresponding to an image target portion.

* * * * *